US007040181B2

(12) United States Patent  
Rieder et al.

(10) Patent No.: US 7,040,181 B2  
(45) Date of Patent: May 9, 2006

(54) CORIOLIS MASS MEASURING DEVICE

(75) Inventors: Alfred Rieder, Landshut (DE);  
Wolfgang Drahm, Freising (DE);  
Michael Fuchs, Eschbach (DE);  
Hans-Jörg Sprich, Schopfheim (DE);  
Ibho Itin, Liestal (CH); Samuel Wyss, Basel (CH)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 11/084,507

(22) Filed: Mar. 21, 2005

(65) Prior Publication Data

US 2005/0229719 A1 Oct. 20, 2005

Related U.S. Application Data

(60) Provisional application No. 60/570,490, filed on May 13, 2004, provisional application No. 60/556,491, filed on Mar. 26, 2004.

(30) Foreign Application Priority Data

Mar. 19, 2004 (DE) .................. 10 2004 014 029  
Apr. 30, 2004 (DE) .................. 10 2004 021 690

(51) Int. Cl.  
*G01F 1/84* (2006.01)

(52) U.S. Cl. .................. 73/861.357

(58) Field of Classification Search .................. None  
See application file for complete search history.

(56) References Cited

U.S. PATENT DOCUMENTS 4,187,721 A 2/1980 Smith  
4,491,025 A 1/1985 Smith  
4,524,610 A * 6/1985 Fitzgerald et al. ......... 73/54.25

(Continued)

FOREIGN PATENT DOCUMENTS

EP 0 553 939 A2 8/1993

(Continued)

*Primary Examiner*—Harshad Patel  
(74) *Attorney, Agent, or Firm*—Bacon & Thomas

(57) ABSTRACT

A Coriolis mass flow measuring device includes a vibratory measuring transducer having at least one measuring tube, which has medium flowing through it during operation. In operation, the measuring tube is caused by an exciter arrangement to undergo mechanical oscillations, especially bending oscillations. Additionally, the Coriolis mass flow measuring device includes a sensor arrangement for producing oscillation measurement signals ($s_1$, $S_2$) representing the inlet-end and outlet-end oscillations of the measuring tube. Measuring device electronics controlling the exciter arrangement produces an exciter current ($i_{exc}$) and an intermediate value ($X'_m$) derived from the oscillation measurement signals ($s_1$, $s_2$). This intermediate value represents an uncorrected mass flow. Derived from the exciter current and/or from a component of the exciter current ($i_{exc}$), an intermediate value ($X_2$) is produced, which corresponds to a damping of the oscillations of the measuring tube. This damping is especially a function of an apparent viscosity, and/or a viscosity-density product, of the medium guided in the measuring tube. Furthermore, a correction value ($X_K$) is produced for the intermediate value ($X'_m$) utilizing the intermediate value ($X_2$) and a viscosity measurement value ($X_\eta$) determined initially or during operation. The viscosity measurement value ($X_\eta$) corresponds to a viscosity of the medium guided in the measuring tube and/or to a predetermined reference viscosity. On the basis of the intermediate value ($X'_m$) and the correction value ($X_K$), the measuring device electronics then produces an exact mass flow rate measurement value ($X_m$).

19 Claims, 7 Drawing Sheets

U.S. PATENT DOCUMENTS

| | | | |
|---|---|---|---|
| 4,660,421 A | 4/1987 | Dahlin et al. | |
| 4,733,569 A | 3/1988 | Kelsey et al. | |
| 4,801,897 A * | 1/1989 | Flecken | 73/861.357 |
| 4,876,898 A | 10/1989 | Cage et al. | |
| 5,069,074 A | 12/1991 | Young et al. | |
| 5,218,873 A | 6/1993 | Lang | |
| 5,253,533 A | 10/1993 | Lam et al. | |
| 5,301,557 A | 4/1994 | Cage et al. | |
| 5,448,921 A | 9/1995 | Cage et al. | |
| 5,531,126 A | 7/1996 | Drahm | |
| 5,602,345 A | 2/1997 | Wenger et al. | |
| 5,602,346 A | 2/1997 | Kitami et al. | |
| 5,616,868 A | 4/1997 | Hagenmeyer et al. | |
| 5,796,011 A | 8/1998 | Keita et al. | |
| 5,869,770 A | 2/1999 | Yoshimura et al. | |
| 6,006,609 A | 12/1999 | Drahm et al. | |
| 6,378,364 B1 * | 4/2002 | Pelletier et al. | 73/152.47 |
| 6,505,519 B1 * | 1/2003 | Henry et al. | 73/861.356 |
| 6,513,393 B1 | 2/2003 | Eckert et al. | |
| 6,651,513 B1 | 11/2003 | Wenger | |
| 6,691,583 B1 | 2/2004 | Rieder et al. | |
| 2001/0039839 A1 | 11/2001 | Wenger | |
| 2002/0184940 A1 | 12/2002 | Storm, Jr. | |
| 2003/0056574 A1 | 3/2003 | Drahm | |
| 2003/0208325 A1 | 11/2003 | Keilty | |
| 2003/0233878 A1 | 12/2003 | Drahm | |
| 2004/0221660 A1 | 11/2004 | Dutton | |
| 2005/0022611 A1 | 2/2005 | Hemp | |
| 2005/0081643 A1 | 4/2005 | Mattar | |

FOREIGN PATENT DOCUMENTS

| | | |
|---|---|---|
| EP | 1 001 254 A1 | 5/2000 |
| EP | 1 281 938 A2 | 2/2003 |
| EP | 1 291 639 A1 | 3/2003 |
| WO | WO 88/03261 | 5/1988 |
| WO | WO 93/01472 | 1/1993 |
| WO | WO 95/16897 | 6/1995 |
| WO | WO 97/03339 | 1/1997 |
| WO | WO 98/07009 | 2/1998 |
| WO | WO 99/39164 | 8/1999 |
| WO | WO 00/36379 | 6/2000 |
| WO | WO 00/57141 | 9/2000 |
| WO | WO 01/33174 A1 | 5/2001 |
| WO | WO 02/37063 A2 | 5/2002 |
| WO | WO 03/076880 A1 | 9/2003 |
| WO | WO 03/095949 A1 | 11/2003 |
| WO | WO 03/095950 A1 | 11/2003 |

* cited by examiner

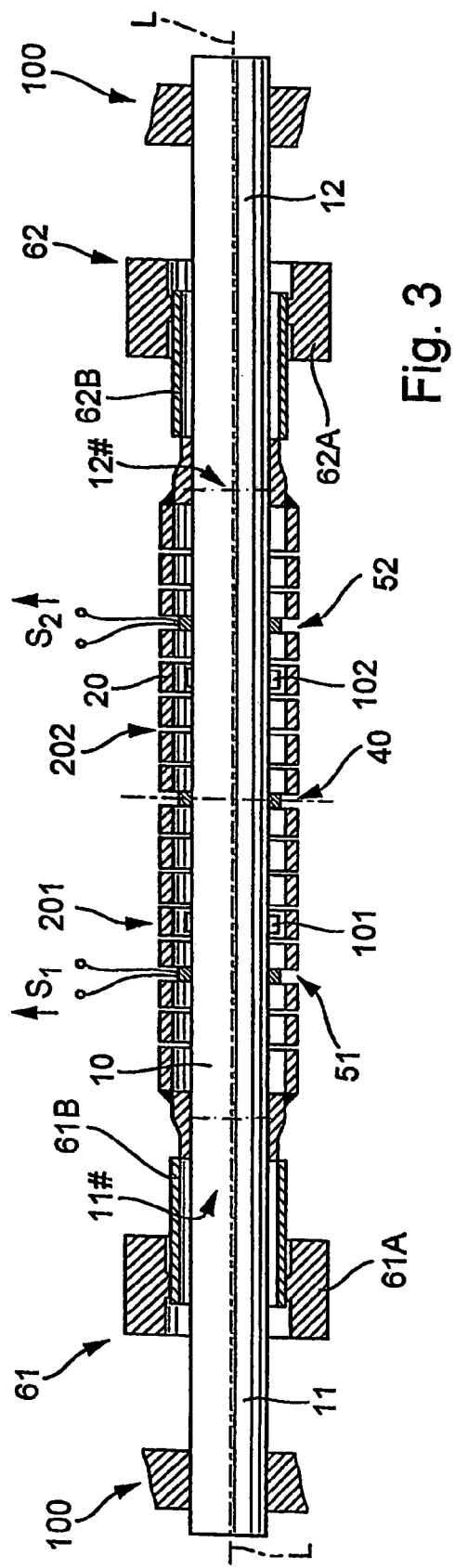
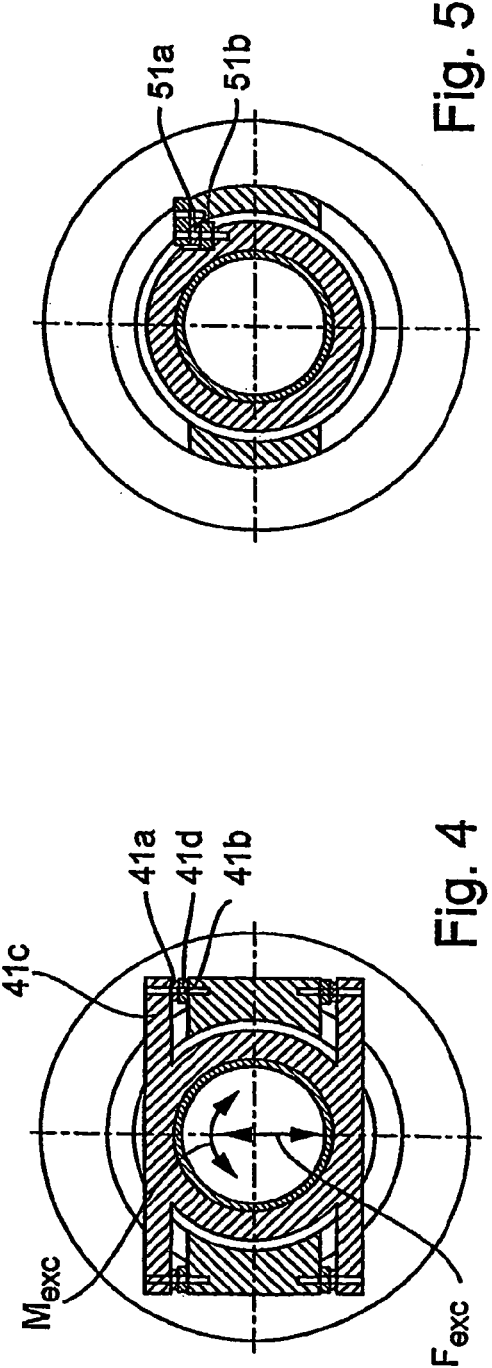

CORIOLIS MASS MEASURING DEVICE

FIELD OF THE INVENTION

The invention relates to a Coriolis mass flow/density meter for a medium, particularly a medium of two or more phases, flowing in a pipeline, as well as to a method for producing a measurement value representing mass flow.

BACKGROUND OF THE INVENTION

In the technology of process measurements and automation, for the measurement of physical parameters of a medium flowing in a pipeline, parameters such as e.g. mass flow rate, density and/or viscosity, it is common to use such in-line measuring devices, especially Coriolis mass flow measuring devices, which use a vibratory transducer inserted into the course of the pipeline conducting the medium and traversed by the medium during operation, and a measuring and operating circuit connected thereto, to produce reaction forces in the medium, forces such as e.g. Coriolis forces related to the mass flow rate, inertial forces related to the density, and frictional forces related to the viscosity, etc., and to derive from these one or more measurement signals representing the current mass flow rate, the current viscosity and/or the current density of the medium. Such in-line measuring devices having a vibratory transducer, as well as the way in which they operate, are known per se to those skilled in the art and are described extensively and in detail e.g. in WO-A 03/095950, WO-A 03/095949, WO-A 03/076880, WO-A 02/37063, WO-A 01/33174, WO-A 00/57141, WO-A 99/39164, WO-A 98/07009, WO-A 95/16897, WO-A 88/03261, EP-A 1 281 938, EP-A 1 001 254, EP-A 553 939, U.S. Pat. No. 2003/0208325, or the U.S. Pat. Nos. 6,691,583, 6,651,513, 6,513,393, 6,505,519, 6,006,609, 5,869,770, 5,796,011, 5,602,346, 5,602,345, 5,531,126, 5,301,557, 5,253,533, 5,218,873, 5,069,074, 4,876,898, 4,733,569, 4,660,421, 4,524,610, 4,491,025, or 4,187,721.

It is noted that the transducers are also sometimes referenced in the literature as sensors. The term "transducer" is used here, because a herein-discussed component of the transducer also bears the label "sensor".

For guiding the medium, the transducers include always at least one measuring tube held, for example, in a tubular or box-shaped support frame. The measuring tube has a curved or straight tube segment, which is caused to vibrate—driven by an electromechanical exciter arrangement—during operation for producing the above-mentioned reaction forces. For registering vibrations, particularly vibrations at the inlet and outlet ends, of the tube segment, the measuring transducers additionally have electrophysical sensor arrangements reacting to movements of the tube segment. With Coriolis mass flow measuring devices for a medium flowing in a pipeline, the measuring of the mass flow rate is accomplished, for example, by allowing the medium to flow through the measuring tube interposed in the pipeline and oscillating the tube during operation, whereby the medium experiences Coriolis forces. These forces, in turn, effect that the inlet and outlet regions of the measuring tube oscillate with phases which are shifted with respect to one another. The size of this phase shift serves as a measure for the mass flow rate. Then the oscillations of the measuring tube are registered by means of two oscillation sensors of the above-mentioned sensor arrangement separated from one another along length of the measuring tube and are transformed into oscillation measurement signals, from whose mutual phase difference the mass flow rate is derived.

Already the above-referenced U.S. Pat. No. 4,187,721 mentions that also the instantaneous density of the flowing medium is usually measurable with Coriolis mass flow measuring devices, and, indeed, on the basis of a frequency of at least one of the oscillation measurement signals delivered by the sensor arrangement. Moreover, usually a temperature of the medium is also measured directly, in suitable manner, for instance by means of a temperature sensor arranged on the measuring tube. Besides the mass flow rate and/or the density of the medium, Coriolis mass flow measuring devices or other in-line measuring devices with a vibratory transducer can also be used to measure a viscosity and/or a viscosity-density product of the medium flowing in the measuring tube; see, in this connection, particularly the U.S. Pat. Nos. 6,651,513, 5,531,126, 5,253,533, and 4,524,610, or WO-A 95/16897. It can thus be assumed, without more, that, even when not expressly described, modern in-line measuring devices with a vibratory measuring transducer, especially Coriolis mass flow measuring devices, enable measurement also of density, viscosity and/or temperature of the medium, especially considering that these measurements can, in any case, always be used for compensation of measurement errors resulting from fluctuating medium density and/or medium viscosity; see, in this connection, especially the already mentioned U.S. Pat. Nos. 6,513,393, 6,006,609, and 5,602,346, as well as WO-A 02/37063, WO-A 99/39164, and WO-A 00/36379.

In the application of vibratory transducers, it has, however, been found, as also discussed, for instance, in JP-A 10-281846, WO-A 03/076880, and U.S. Pat. No. 6,505,519, that, in the case of inhomogeneous media, especially media of two or more phases, the oscillation measuring signals derived from the oscillations of the measuring tube, especially the mentioned phase shift, are subject to fluctuations to a considerable degree, in spite of keeping viscosity and density of the separate phases, as well as the mass flow rate, constant and/or appropriately taking them into consideration, such that, without remedial measures, the signals can become completely unusable for measuring the desired physical parameter. Such inhomogeneous media can, for example, be liquids, into which, as e.g. practically unavoidable in dosing- or bottling-processes, gas, especially air, present in the pipeline, is entrained, or from which a dissolved medium, e.g. carbon dioxide, outgases and leads to foam formation. Other examples of such inhomogeneous media are emulsions, as well as wet, or saturated, steam. In terms of causes for the problems experienced in the measurement of inhomogeneous media by means of vibratory transducers, one can mention, for example, the unilateral attachment or deposition of gas bubbles or solids particles internally on the wall of the measuring tube, and the so-called "bubble-effect", in which entrained gas bubbles act as flow guides for liquid volume elements accelerated transversely to the measuring tube longitudinal axis.

While a flow, or medium, conditioning, as the case may be, preceding the actual flow measurement is proposed in WO-A 03/076880 for lessening the measurement errors associated with media of two or more phases, JP-A 10-281846 and, also, U.S. Pat. No. 6,505,519, each describe a correcting of the flow measurement, especially mass flow rate measurement, based on oscillation measurement signals, particularly using an evaluation of shortfalls between a highly accurately measured, actual medium density and an apparent medium density determined during operation by means of Coriolis mass flow measurement devices.

In particular, pre-trained, occasionally even adaptive, classifiers of the oscillation measurement signals are proposed for this purpose. The classifiers can be constructed, for example, in the form of a Kohonen map or a neural network, and can perform the correction either on the basis of a few parameters measured during operation, especially the mass flow rate and the density, along with further characteristics derived therefrom, or also by using an interval of the oscillation measurement signals encompassing one or more oscillation periods. The use of such classifiers has, for example, the advantage, that, in comparison to conventional Coriolis mass flow/density meters, no, or only very slight, changes have to be made at the transducer, be it with respect to the mechanical construction, the exciter arrangement, or the operating circuit controlling such, which are adjusted to accommodate the special application. However, there is a significant disadvantage of such classifiers, among other things, in that, compared to conventional Coriolis mass flow measuring devices, considerable changes are required in the realm of measurement value production, especially as regards the analog-to-digital converters and the microprocessors which are used. Thus, as described in the U.S. Pat. No. 6,505,519, such signal evaluation requires, for example in the digitizing of the oscillation measurement signals, which can have an oscillation frequency of around 80 Hz, a sampling rate of about 55 kHz, or more, in order to achieve sufficient accuracy. Said differently, the oscillation measurement signals must be sampled using a sampling ratio significantly above 600:1. On top of this, also the firmware stored and executed in the digital measuring circuit becomes correspondingly complex. An additional disadvantage of such classifiers is to be seen in the fact that they must be trained and correspondingly validated for the measuring conditions actually present during operation of the transducer, be it the conditions of installation, the medium to be measured, and its usually variable properties, or other factors affecting the accuracy of measurement. Due to the high complexity of the interactions of all these factors, the training and its validation can finally usually only be done at the site and individually for each transducer, this, in turn, leading to a considerable expense being associated with the start-up of the transducer. Finally, it has also been found, that such classification algorithms, on the one hand because of the great complexity, and, on the other hand, because of the fact that, usually, a corresponding mathematical physics model with technically relevant or understandable parameters is not explicitly present, classifiers exhibit a very low transparency and are, consequently, often difficult to place. Accompanying this, considerable resistance can arise with customers, with such acceptance problems especially occurring when it concerns classifiers involving a self-adapting mechanism, for instance a neural network.

As another possibility for avoiding the problem with inhomogeneous media, U.S. Pat. No. 4,524,610 proposes, for example, to install the transducer such that the straight measuring tube extends essentially vertically, in order to prevent, as much as possible, an attachment of such interfering, especially gaseous, inhomogeneities. This is, however, a very special solution which cannot always be realized, without more, in industrial process measurement technology. On the one hand, the pipeline, into which the transducer is to be inserted namely for this case, must, on occasion, be fitted to the transducer, and not the reverse, a fact which can mean increased extra expense to the user in creating the measurement location. On the other hand, the measuring tubes can, as already mentioned, be curved, so that the problem cannot always be satisfactorily solved by an adjustment of orientation in the installation. It has also been found, in this connection, that the mentioned corruptions of the measurement signal cannot necessarily be avoided with certainty by the use of a vertically installed, straight measuring tube.

SUMMARY OF THE INVENTION

An object of the invention is to provide a corresponding Coriolis mass flow measuring device that is suited for measuring mass flow rate very accurately, even in the case of inhomogeneous media, especially media of two or more phases, and, indeed, preferably with a measurement error of less than 10% referenced to the actual mass flow rate. A further object is to provide a corresponding method for producing a corresponding mass flow rate measurement value.

For achieving this object, the invention provides a Coriolis mass flow measuring device, especially a Coriolis mass flow/density measuring device, or a Coriolis mass flow/viscosity measuring device, for measuring the mass flow rate of a medium flowing in a pipeline, especially a medium of two or more phases, which Coriolis mass flow measuring device includes a vibratory transducer and a measuring device electronics electrically coupled to the transducer, wherein the transducer has:
at least one measuring tube to be interposed in the pipeline, especially an essentially straight measuring tube, for guiding the medium to be measured and communicating with the connected pipeline,
an exciter arrangement acting on the measuring tube for causing the at least one measuring tube to vibrate with bending oscillations at least at times, and/or at least in part, during operation, as well as
a sensor arrangement for registering vibrations of the at least one measuring tube, which delivers at least one, first oscillation measurement signal representing oscillations of the measuring tube at the inlet end and at least one, second oscillation measurement signal representing oscillations of the measuring tube at the outlet end, and wherein the measuring device electronics
delivers, at least at times, an exciter current driving the exciter arrangement and, at least at times, a mass flow rate measurement value representing a mass flow rate to be measured,
produces a first intermediate value derived from the oscillation measurement signals and corresponding to the mass flow rate to be measured and/or to a phase difference between the two oscillation measurement signals, as well as a second intermediate value derived from the exciter current, and/or from a component of the exciter current, and corresponding to a damping of the oscillations of the measuring tube, especially a damping dependent on an apparent viscosity, and/or a viscosity-density product, of the medium guided in the measuring tube, as well as
uses the second intermediate value and a viscosity measurement value predetermined, or determined during operation, especially by use of the transducer and/or the measuring device electronics, and corresponding to a viscosity of the medium guided in the measuring tube and/or to a previously supplied, reference viscosity, to produce a correction for the first intermediate value, and, on the basis of the first intermediate value and the correction, the mass flow rate measurement value.

Additionally, the invention resides in a method for measuring a mass flow rate of a medium, especially a medium of two or more phases, flowing in a pipeline, using a Coriolis mass flow measuring device having a vibratory transducer and a measuring device electronics electrically coupled with the transducer, which method includes the following steps:

flowing the medium to be measured through at least one measuring tube of the transducer communicating with the pipeline and feeding an exciter current into an exciter arrangement mechanically coupled with the measuring tube guiding the medium for causing mechanical oscillations of the measuring tube, especially bending oscillations, letting the measuring tube vibrate in an oscillation mode suited for producing Coriolis forces in the medium flowing therethrough, registering vibrations of the measuring tube and producing a first oscillation measurement signal representing inlet-end oscillations and a second oscillation measurement signal representing outlet-end oscillations, developing, using the two oscillation measurement signals, a first intermediate value corresponding to the mass flow rate to be measured and/or to a phase difference between the two oscillation measurement signals, determining a second intermediate value derived from the exciter current and corresponding to a damping of the oscillations of the measuring tube dependent on an apparent viscosity, and/or a viscosity-density product, of the medium guided in the measuring tube, producing a correction value for the first intermediate value by means of the second intermediate value and by means of an initially determined viscosity measurement value, especially by use of the transducer and/or the measuring device electronics, corresponding to a viscosity of the medium guided in the measuring tube, as well as correcting the first intermediate value by means of the correction value and producing a mass flow rate measurement value representing the mass flow rate to be measured.

In a first development of the Coriolis mass flow measuring device of the invention, the correction value represents a deviation of the viscosity of the medium from an apparent viscosity of the medium guided in the measuring tube, determined during operation on the basis of the exciter current and/or a component of the exciter current, and/or from a viscosity-density product of the medium guided in the measuring tube, determined during operation on the basis of the exciter current.

In a second development of the Coriolis mass flow measuring device of the invention, the measuring device electronics determines the correction value on the basis of a comparison of the second intermediate value with the viscosity measurement value and/or on the basis of a difference existing between the second intermediate value and the viscosity measurement value.

In a third development of the Coriolis mass flow measuring device of the invention, the measuring device electronics produces the second intermediate value also using at least one of the oscillation measurement signals.

In a fourth development of the Coriolis mass flow measuring device of the invention, the exciter arrangement causes the measuring tube to execute torsional oscillations during operation at least at times and/or at least in part, especially torsional oscillations alternating with the bending oscillations, or superimposed over time on the bending oscillations, about an imaginary longitudinal axis of the measuring tube essentially aligned with the measuring tube, especially a principle axis of inertia of the measuring tube, and the measuring device electronics determines also the viscosity measurement value on the basis of the exciter current driving the exciter arrangement and/or on the basis of a component of the exciter current.

In a fifth development of the Coriolis mass flow measuring device of the invention, the measuring tube, driven by the exciter arrangement, executes torsional oscillations having a measuring tube torsional oscillation frequency arranged to be different from a measuring tube lateral oscillation frequency with which the measuring tube, driven by the exciter arrangement, executes lateral oscillations, especially bending oscillations.

In a sixth development of the Coriolis mass flow measuring device of the invention, the measuring device electronics also produces the viscosity measurement value.

In a seventh development of the Coriolis mass flow measuring device of the invention the measuring device electronics delivers a density measurement value derived from the first and/or the second oscillation measurement signal and representing a density of the medium, and the measuring electronics determines the correction value, especially the viscosity measurement value, also on the basis of the density measurement value.

In an eighth development of the Coriolis mass flow measuring device of the invention, the measuring device electronics is coupled with an external viscosity measurement device, especially a viscosity measuring device located remotely from the Coriolis mass flow measuring device, and the viscosity measurement device delivers the viscosity measurement value at least at times.

In a ninth development of the Coriolis mass flow measuring device of the invention, the measuring device electronics is coupled, at least at times, with a differential pressure sensor, which, at least at times, delivers a differential pressure measurement value representing a pressure difference over a length of the pipeline.

In a tenth development of the Coriolis mass flow measuring device of the invention, the measuring device electronics determines, at least at times and on the basis of the exciter current and/or on the basis of a component of the exciter current, as well as with the use of the viscosity measurement value, a concentration measurement value, which represents a volume, and/or mass, fraction, especially a relative volume, and/or mass, fraction, of a phase in a two- or more-phase medium in the measuring tube.

In an eleventh development of the Coriolis mass flow measuring device of the invention, the measuring tube communicates with the connected pipeline through an inlet fitting opening into an inlet end and an outlet fitting opening into an outlet end, and the transducer includes, fixed at the inlet and outlet ends of the measuring tube, especially mechanically coupled with the exciter arrangement, a counter-oscillator, which vibrates at least at times during operation, especially with phase opposite to that of the measuring tube.

In a twelfth development of the Coriolis mass flow measuring device of the invention, the Coriolis mass flow measuring device is used for measuring a mass flow of a two- or more-phase medium flowing in a pipeline, especially a liquid-gas mixture.

In a first development of the method of the invention, the method further includes the step of actuating bending oscillations in the measuring tube for producing Coriolis forces in the medium flowing through the measuring tube.

In a second development of the method of the invention, the method further includes the step of actuating torsional oscillations in the measuring tube, especially torsional oscillations superimposed on the bending oscillations, as well as the step of determining a second intermediate value on the basis of the exciter current and/or at least a component of the exciter current actuating the torsional oscillations of the measuring tube.

In a third development of the method of the invention, the step of producing the correction value for the intermediate value further includes the step of comparing the second intermediate value with the viscosity measurement value and/or determining a difference between the second intermediate value and the viscosity measurement value, as well as the step of determining a deviation of the viscosity of the medium from an apparent viscosity of the medium guided in the measuring tube, determined during operation on the basis of the exciter current, and/or from a viscosity-density product of the medium guided in the measuring tube, determined during operation on the basis of the exciter current.

In a fourth development of the method of the invention, the method further includes the step of developing a second measurement value representing a density of the medium on the basis of the oscillation measurement signals, as well as the step of developing a correction value on the basis of the second measurement value.

In a fifth development of the method of the invention, the method is used for calibrating a Coriolis mass flow measuring device and/or a vibratory transducer having at least one measuring tube.

The invention rests particularly on the recognition that the exciter power fed into the transducer for maintaining the lateral oscillations of the measuring tube can be influenced to a great degree by inhomogeneities in the medium to be measured, homogeneities such as e.g. entrained gas bubbles, entrained solid particles, and the like. If this exciter power, dependent on an apparent viscosity and/or a viscosity-density product of the medium guided in the measuring tube, is compared with an actual, or at least significantly more accurately measured, viscosity of the medium, obtained, for example, by a corresponding external and/or internal reference-measurement, the part instantaneously relevant for the mass flow measurement attributable to inhomogeneities in the medium can be estimated with sufficient accuracy. A special advantage of the invention is that even the reference measurement of the viscosity can be performed by means of the same Coriolis mass flow measuring device and, consequently, independently of possible external measurement locations.

A further advantage of the invention is that, in the case of the Coriolis mass flow measuring device of the invention, as compared to a conventional device, there is need for small changes only in the usually digital measurement production, essentially limited to the firmware, while, both in the case of the transducer and also in the case of the production and pre-processing of the oscillation measurement signals, no, or only very slight, changes are required. Thus, for example, the oscillation measurement signals can be sampled, as before, with a usual sampling ratio of far below 100:1, especially about 10:1.

BRIEF DESCRIPTION OF THE DRAWINGS

The invention and further advantageous developments thereof will now be explained in greater detail on the basis of examples of embodiments presented in the figures of the drawing. Equal parts are given the same reference characters in all figures; when required for clarity, already mentioned reference characters are omitted in subsequent drawings.

FIG. 3 shows the transducer of FIG. 2 in a side view, FIG. 4 shows the transducer of FIG. 2 in a first cross section, FIG. 5 shows the transducer of FIG. 2 in a second section.

DESCRIPTION OF THE PREFERRED EMBODIMENTS

Figure 1:
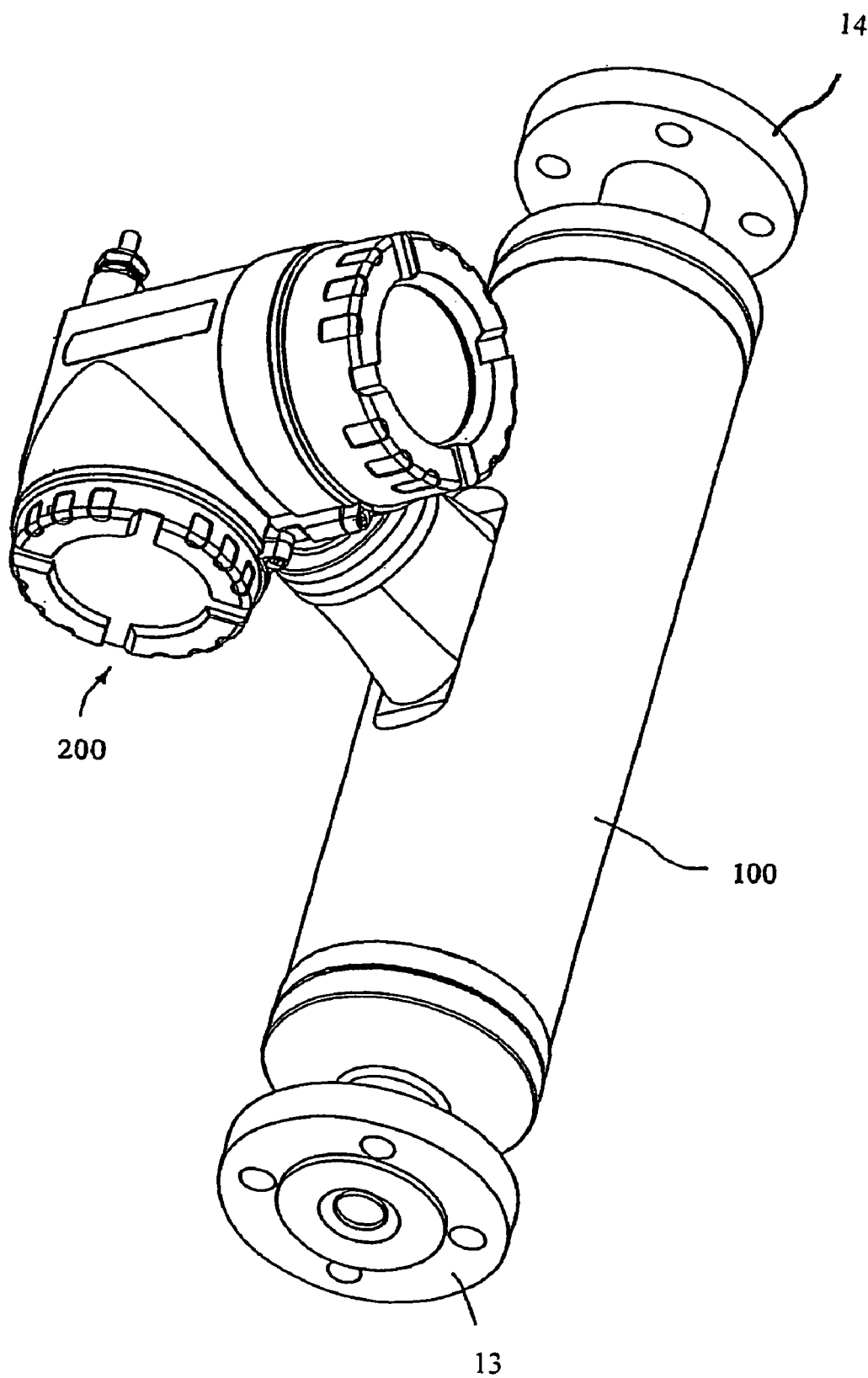
FIG. 1 shows a Coriolis mass flow measuring device which can be inserted in a pipeline for measuring a mass flow rate of a fluid flowing in the pipeline.

While the invention is susceptible to various modifications and alternative forms, exemplary embodiments thereof have been shown by way of example in the drawings and will herein be described in detail. It should be understood, however, that there is no intent to limit the invention to the the particular forms diclosed, but on the contrary, the intention is to cover all modifications, equivalents, and alternatives falling within the spirit and scope of the invention as defined by the intended claims.

FIG. 1 is a perspective illustration of a Coriolis mass flow measuring device 1 for registering a mass flow rate m of a medium flowing in a pipeline (not shown) and for reflecting such in the form of a mass flow rate measurement value $X_m$ instantaneously representing this mass flow rate. The medium can be practically any flowable material, for example a liquid, a gas, a vapor, or the like. Moreover, the Coriolis mass flow measurement device 1 can, on occasion, also be used for measuring a density $\rho$ and/or a viscosity $\eta$ of the medium.

Figure 2:
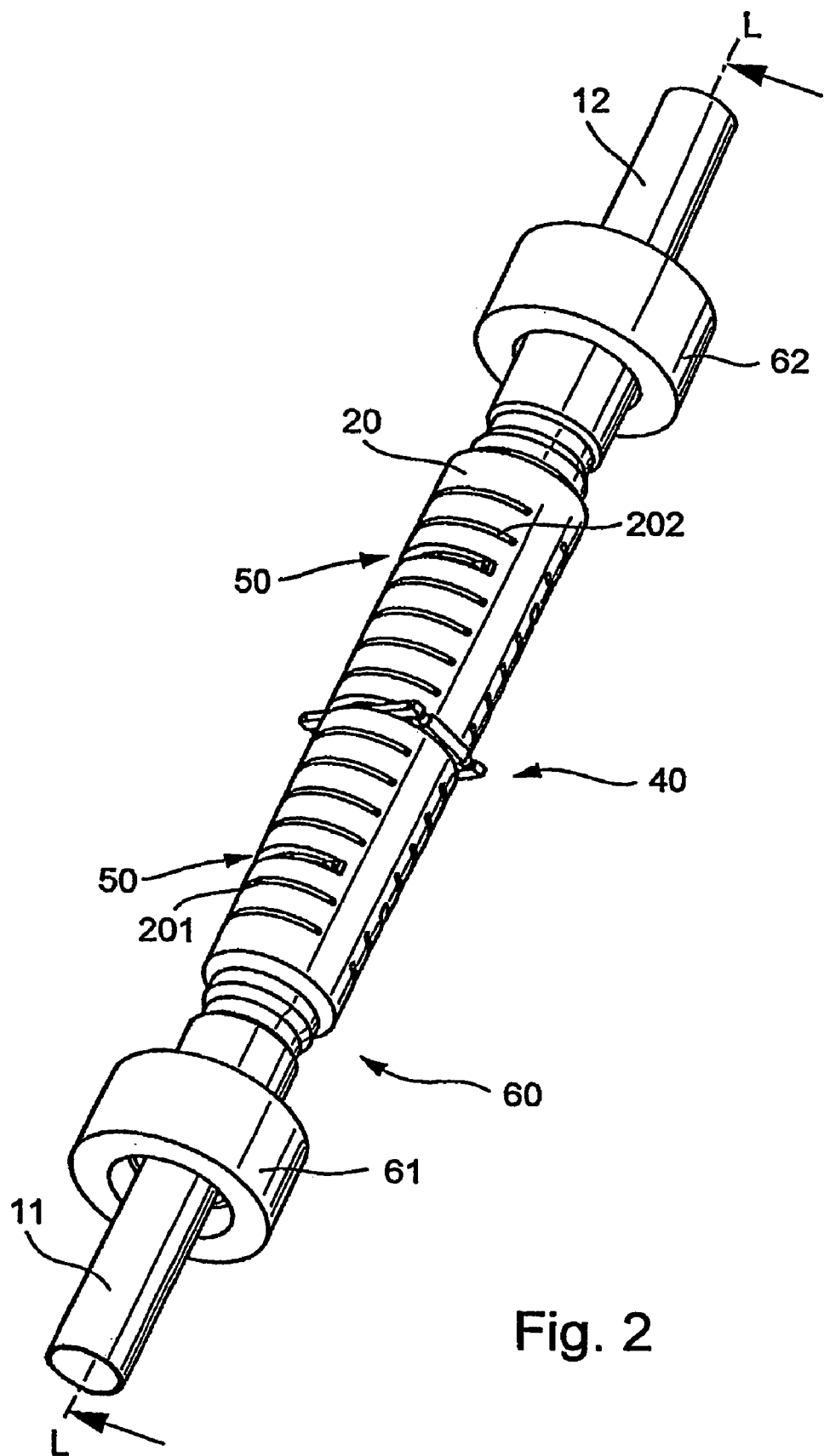
FIG. 2 shows, in perspective side view, an embodiment of a vibratory transducer suited for the measuring device of FIG. 1.
Figure 6:
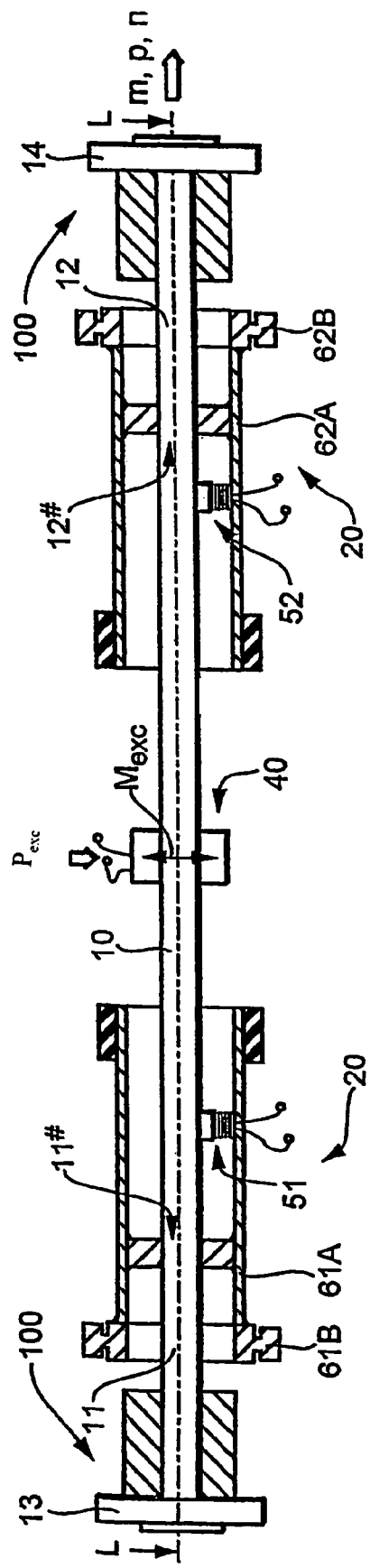
FIG. 6 shows a longitudinally sectioned, side view of a further embodiment of a vibratory transducer suited for the Coriolis mass flow measuring device of FIG. 1.
Figure 7:
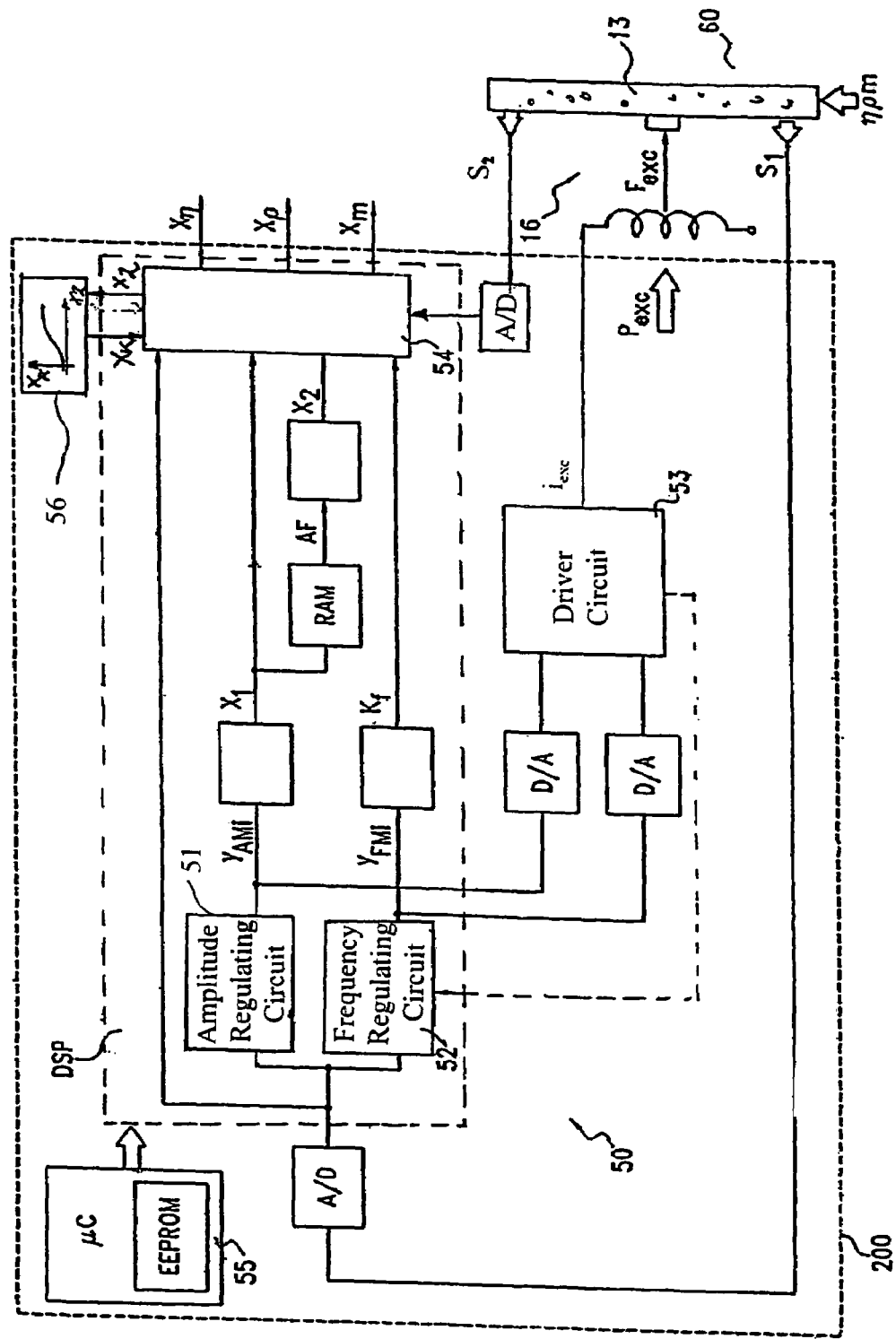
FIG. 7 shows schematically in the form of a block diagram a preferred development of a measuring device electronics for the Coriolis mass flow measuring device of FIG. 1, and FIGS. 8, 9 are graphs of measurement data experimentally determined with a Coriolis mass flow measuring device according to the FIGS. 1 to 7.

The Coriolis mass flow measuring device 1 includes for these goals a vibratory measuring transducer 10, through which the medium to be measured flows during operation, and a measuring device electronics 50 electrically connected with the transducer 10. Examples of embodiments and developments of the transducer are shown in FIGS. 2 to 6, while FIGS. 2 and 7 are schematic illustrations of examples of the measuring device electronics. Preferably, the measuring device electronics 50 is additionally so designed that it can exchange measurement and/or other operational data with a measurement value processing unit superordinated thereto, for example a programmable logic controller (PLC), a personal computer and/or a work station, via a data transmission system, for example a field-bus system. Additionally, the measuring device electronics 50 is so designed that it can be fed from an external power supply, for example also over the above-mentioned field-bus system. For the case in which the vibration-type measuring device is to be coupled to a field bus or some other communication system, the measuring device electronics 50, especially a programmable one, has a corresponding communications interface, e.g. for the sending of the measurement data to the already mentioned programmable logic controller or to a superordinated process control system. For accommodating the measuring device electronics 50, an electronics housing 200 is additionally provided, either directly mounted, especially externally, on the transducer 10, or else removed from such to some other location.

As already mentioned, the measuring device includes a vibratory measuring transducer 10, through which the medium to be measured flows during operation and which serves for producing in a medium flowing therethrough such mechanical reaction forces, especially Coriolis forces dependent on the mass flow rate, inertial forces dependent on medium density and/or frictional forces dependent on medium viscosity, forces which react measurably on the transducer, especially those capable of being registered by a sensor. On the basis of these reaction forces characterizing the medium, e.g. the flow rate, the density and/or the viscosity of the medium can be measured, in ways known to those skilled in the art.

FIGS. 3 and 4 show schematically a mechanical-electrical converter arrangement serving as an illustrative embodiment of a vibratory transducer 10. The mechanical construction and the functioning of such a converter arrangement is know per se to those skilled in the art and described in detail e.g. also in U.S. Pat. No. 6,691,583, and in WO-A 03/095949 or WO-A 03/095950.

For guiding the medium and for producing said reaction forces, the transducer includes at least one, essentially straight measuring tube 10 of predeterminable diameter, which, during operation, is caused, at least at times, to vibrate with one or more frequencies, thereby undergoing repeated elastic deformations. Elastic deformation of the measuring tube lumen means here that a spatial shape and/or a spatial position of the tube lumen is cyclically, especially periodically, changed in predeterminable manner within the elastic range of the measuring tube 10. See, in this connection, also the U.S. Pat. Nos. 4,801,897, 5,648,616, 5,796,011, 6,066,609 and 6,691,583, the WO-A 03/095949 and/or the WO-A 03/095950. It should be noted here that, although the transducer includes in this embodiment only a signal, straight measuring tube, a large number of other Coriolis mass flow transducers described in the state of the art can be used instead of the illustrated transducer. In particular, for example, vibratory transducers having two, parallel, straight measuring tubes traversed by the medium to be measured are suitable, such as are described in detail, for example, also in the U.S. Pat. No. 5,602,345.

Measuring tube 10, which communicates in the usual manner with the pipeline supplying, respectively receiving, the medium to be measured, is mounted for oscillation in a rigid, especially bending- and twisting-resistant, support frame 14. Instead of the tube-shaped support frame 14 extending coaxially with the measuring tube, as shown here, of course, other suitable support means, such as e.g. tubes extending parallel to the measuring tube, or box-shaped structures, can be used. For causing the medium to flow through, the measuring tube 10 is connected to the pipeline by way of an inlet tube piece 11 opening into an inlet end 11# and by way of an outlet tube piece 12 opening into an outlet end 12#. Measuring tube 10, and the inlet- and outlet-tube pieces 11, 12, are, as much as possible, aligned with one another and with an imaginary measuring tube longitudinal axis L and are preferably provided as one piece, so that, for their production, e.g. a single, tube-shaped workpiece can be used; if necessary, measuring tube 10 and the tube pieces 11, 12 can, however, also be manufactured by means of separate, later-joined, e.g. welded together, workpieces. For manufacture of the measuring tube 10, as well as also the inlet and outlet tube pieces 11, 12, practically any material commonly used for such transducers can be used, such as e.g. iron-, titanium-, zirconium- and/or tantalum-alloys, synthetic materials, or ceramics. For the case where the transducer is to be releasably assembled with the pipeline, the inlet tube piece 11 and the outlet tube piece 12 are each provided with respective first and second flanges 13, 14; if necessary, however, the inlet and outlet tube pieces 11, 12 can also be directly connected with the pipeline, e.g. by means of welding or brazing. Additionally, as schematically illustrated in FIG. 1, a transducer housing 100 is provided, fixed to the inlet and outlet tube pieces 11, 12 and enclosing the measuring tube 10; compare FIGS. 1 and 2 in this connection.

For measuring the mass flow rate, the measuring tube 10 is excited to oscillate in a first oscillation mode, the so-called useful mode, in which it, at least in part, executes oscillations, especially bending oscillations, laterally to the longitudinal axis L of the measuring tube, especially such that it bends laterally outwards, essentially oscillating at a natural bending eigenfrequency, according to a natural, first form of eigenoscillation, i.e. natural oscillation. Natural eigenfrequencies of such lateral oscillation modes of measuring tubes are, as is known, also dependent, to a special degree, on the density ρ of the medium.

For the case in which the medium in the connected pipeline is flowing and, consequently, the mass flow rate m is different from zero, Coriolis forces are induced in the flowing medium by means of the measuring tube 10 oscillating in the useful mode. These forces, in turn, have an effect on the measuring tube 10, such that, in manner known to those skilled in the art, an additional deformation of the measuring tube 10 is coplanarly superimposed on the first form of eigenoscillation. This deformation, which is essentially on the basis of a natural, second form of eigenoscillation, can be registered by sensors. The instantaneous deflection of the deformation of the measuring tube 10 is, it so happens, especially as concerns its amplitude, also dependent on the instantaneous mass flow rate m. The second form of eigenoscillation, the so-called Coriolis mode, can be e.g., as usual in the case of such transducers, anti-symmetric forms of bending oscillations with two oscillation anti-nodes, or with four oscillation anti-nodes.

In one development of the invention, the measuring tube 10 is excited for producing mass flow dependent Coriolis forces in the flowing medium at least at times with a lateral oscillation frequency $f_{excL}$, which corresponds as exactly as possible to a lowest natural bending eigenfrequency of the measuring tube 10, so that thus the laterally oscillating measuring tube 10, when not yet containing flowing medium, is bent outwards essentially symmetrically with reference to a central axis perpendicular to the longitudinal axis L of the measuring tube and, in this case, shows a single oscillating anti-node. This lowest bending eigenfrequency can, for example, lie at about 850 Hz to 900 Hz in the case of a measuring tube 10 of stainless steel with a nominal breadth of 20 mm, a wall thickness of about 1.2 mm and a length of about 350 mm, plus the usual appendages.

In another development of the invention, the measuring tube 10 is excited for producing viscosity-dependent shear forces in the flowing medium, at least at times, especially simultaneously with the lateral oscillations of the useful mode, with a torsional oscillation frequency fexcT, which correspond as exactly as possible to a natural torsional eigenfrequency of the measuring tube 10, such that it is forced to twist essentially according to a natural form of torsional oscillation about its longitudinal axis; see, in this connection, e.g. also the U.S. Pat. Nos. 4,524,610, 5,253, 533, 6,006,609, or the EP-A 1 158 289. A lowest torsional eigenfrequency can, for example, lie, in the case of a straight measuring tube, about in the range of twice the lowest bending eigenfrequency.

As already indicated, the oscillations of the measuring tube 10 are, on the one hand, damped by a sensor-registered energy loss to the medium, especially for the purpose of viscosity measurement. On the other hand, however, oscillatory energy can also be extracted from the vibrating measuring tube, in that components mechanically coupled thereto, such as e.g. the transducer housing 100 or the attached pipeline, are likewise excited to oscillate. While the, although undesired, energy loss to the transducer housing 100 might, in fact, be calibratable, at least the energy loss into the surroundings of the transducer, particularly to the pipeline, occurs in a manner which is not reproducible, for practical purposes, and may even be unpredictable. For the purpose of suppressing or preventing a possible loss of oscillation energy to the surroundings, a counter-oscillator 20 is therefore additionally provided in the transducer, fixed at the inlet and outlet ends of the measuring tube 10. The counter-oscillator is, as schematically shown in FIG. 2, preferably built in one piece. If necessary, the counter-oscillator 20 can also, as shown in U.S. Pat. No. 5,969,265, EP-A 317 340 or WO-A 00 14 485, be composed of multiple parts or realized by means of two, separate, counter-oscillator segments fixed at the inlet and outlet ends of the measuring tube 10; see FIG. 6. The counter-oscillator 20 serves, among other things, to dynamically balance the transducer for a density value of the medium expected to occur most frequently in the operation of the transducer, or even a critical medium density value, to the extent that transverse forces and/or bending moments possibly arising in the vibrating measuring tube 10 are, for the most part, compensated; see, in this connection, U.S. Pat. No. 6,691, 583. Beyond this, the counter-oscillator 20 serves in the above-described case, where the measuring tube is also excited to torsional oscillations, additionally to produce counter-torsional moments largely compensating such torsional moments produced by the single measuring tube 10 twisting preferably about its longitudinal axis L, thus keeping the surroundings of the transducer, especially the attached pipeline, largely free of dynamic torsional moments. The counter-oscillator 20 can, as schematically show in FIGS. 2 and 3, be provided in tube shape and, for example, be so connected at the inlet end 11# and the outlet end 12# of the measuring tube 10, that it is, as shown in FIG. 3, essentially coaxial with the measuring tube 10. Material for the counter-oscillator 20 can, for practical purposes, be those usable for the measuring tube 10, thus, for example, stainless steel, titanium alloys, etc.

In addition, the transducer 1 has, surrounding the measuring tube 10 and counter-oscillator 20, a transducer housing 100, which protects these components from damaging environmental influences and/or damps possible emissions of sound from the transducer to the surroundings. The transducer housing 100 is, in the embodiment shown here, fixed to an inlet end of the inlet tube piece and to an outlet end of the outlet tube piece, in such a way that measuring tube and counter-oscillator remain capable of oscillation in the transducer housing 100. Additionally, the transducer housing 100 is provided with a neck-like transition piece, on which the electronics housing 200 housing the measuring device electronics 50 is fixed; see FIG. 1.

The counter-oscillator 20, which, especially in comparison to the measuring tube 10, is somewhat less torsionally and/or bending elastic, is caused likewise to oscillate during operation, and, indeed, at essentially the same frequency, but out of phase, especially with opposite phase, as compared to the measuring tube 10. In keeping with this, the counter-oscillator 20 is tuned to have at least one of its torsional eigenfrequencies as accurately as possible equal to one of those torsional frequencies at which the measuring tube 10 is caused mostly to oscillate during operation. Beyond this, the counter-oscillator 20 is adjusted as accurately as possible in at least one of its bending eigenfrequencies to equal at least one bending oscillation frequency with which the measuring tube 10, especially in the useful mode, is caused to oscillate and the counter-oscillator 20 is excited during operation of the measuring transducer also to lateral oscillations, especially bending oscillations, which are developed essentially coplanarly with respect to lateral oscillations of the measuring tube 10, especially the bending oscillations of the useful mode.

In a development of the invention, as schematically shown in FIG. 3, grooves 201, 202 are provided, worked into the counter-oscillator, for enabling, in simple manner, an exact adjustment of its torsional eigenfrequencies, especially a lowering of the torsional eigenfrequencies by lowering a torsional stiffness of the counter-oscillator 20. Although the grooves 201, 202 are shown in FIGS. 2 and 3 as being essentially uniformly distributed in the direction of the longitudinal axis L, they can, if necessary, of course be arranged also non-uniformly distributed in the direction of the longitudinal axis L. Beyond this, the mass distribution of the counter-oscillator can, as likewise shown schematically in FIG. 3, also be corrected by means of corresponding mass balancing bodies 101, 102, which are fixed on the measuring tube 10. The mass balancing bodies 101, 102 can e.g. be metal rings pushed onto the measuring tube 10, or metal platelets fixed to such.

For producing mechanical oscillations of the measuring tube 10, the transducer includes, additionally, an exciter arrangement 40, especially an electrodynamic exciter arrangement, coupled to the measuring tube. The exciter arrangement 40 serves for converting an electrical exciter power $P_{exc}$ fed from the measuring electronics, e.g. with a regulated exciter current $i_{exc}$ and/or a regulated voltage, into an exciter moment $M_{exc}$ acting e.g. in the form of a pulse, or harmonically, on, and elastically deforming, the measuring tube 10 and/or into an exciter force $F_{exc}$ acting laterally on the measuring tube 10. For achieving a highest possible efficiency and a highest possible signal/noise ratio, the exciter power $P_{exc}$ is set as accurately as possible such that principally the oscillations of the measuring tube 10 in the useful mode are maintained, and, indeed, as accurately as possible at an instantaneous eigenfrequency of the measuring tube containing the flowing medium. The exciter force $F_{exc}$, and also the exciter moment $M_{exc}$, can, in this case, as, in fact, shown schematically in FIGS. 4 and 6, each be in bi-directional form, or, however, also in uni-directional form, and are, in manner known to those skilled in the art, tuned as regards their amplitude e.g. by means of a current and/or voltage regulating circuit and as regards their frequency e.g. by means of a phase-locked loop.

The exciter arrangement 40 can, as usual for such vibratory transducers, be, for example, a plunger coil arrangement having attached to the counter-oscillator 20, or to the inside of the transducer housing 100, a cylindrical exciter coil, which conducts an appropriate exciter current $i_{exc}$ during operation, and having inserted at least partially in the exciter coil a permanently magnetic armature fixed to the measuring tube 10. Furthermore, the exciter arrangement 40 can also be realized by means of multiple plunger coils, as shown e.g. in the U.S. Pat. No. 4,524,610 or in WO-A 03/09950, or also by means of electromagnets.

For detecting the oscillations of the measuring tube 10, the transducer additionally includes a sensing arrangement 60, which produces by means of at least one, first oscillation sensor 17 reacting to vibrations of the measuring tube 10 an oscillation measurement signal $s_1$, especially an analog signal, representing the vibrations. The oscillation sensor 17 can e.g. be formed by means of a permanently magnetic armature, which is fixed to the measuring tube 10 and which interacts with a sensor coil mounted on the counter-oscillator 20 or on the transducer housing. Especially suited as oscillation sensor 17 are those sensors that are based on the electrodynamic principle and register a velocity of the deflections of the measuring tube 10. Acceleration-measuring, electrodynamic, or even travel-measuring, resistive or optical, sensors can, however, also be used. Of course, also other sensors known to those skilled in the art and suited for the detection of such vibrations can be used. The sensing arrangement 60 includes, additionally, a second oscillation sensor 18, especially one identical to the first oscillation sensor 17, by means of which it delivers a second oscillation measurement signal $s_2$ likewise representing vibrations of the measuring tube 10. The two oscillation sensors in this embodiment are arranged separated from one another along the length of the measuring tube 10, especially at equal distances from the middle of the measuring tube 10, such that the sensing arrangement 60 locally registers both the inlet- and the outlet-end vibrations of the measuring tube 10 and transduces them into the corresponding oscillation measurement signals $s_1$ and $s_2$. Both oscillation measurement signals $s_1$, $s_2$, which usually each exhibit a signal frequency corresponding to an instantaneous oscillation frequency of the measuring tube 10, are, as shown in FIG. 7, fed to the measuring device electronics 50, where they are, in manner known to those skilled in the art, pre-processed, especially digitized, and subsequently suitably evaluated.

In an embodiment of the invention, the exciter arrangement 40 is, as also shown in FIGS. 2 and 3, so constructed and arranged in the transducer that it acts in operation simultaneously, especially differentially, on the measuring tube 10 and on the counter-oscillator 20. In the case of this further development of the invention, the exciter arrangement 40 is, as also shown in FIG. 2, advantageously so constructed and so arranged in the transducer, that it acts in operation simultaneously, especially differentially, on the measuring tube 10 and on the counter-oscillator 20. In the embodiment shown in FIG. 4, the exciter arrangement 40 has a first exciter coil 41a, which, in operation, contains, at least at times, the exciter current, or an exciter current component. The exciter coil 41a is fixed to a lever 41c connected to the measuring tube 10 and, by way of the lever and an armature 41b fixed from the outside to the counter-oscillator 20, acts differentially on the measuring tube 10 and the counter-oscillator 20. The arrangement has, among other things, also the advantage that, on the one hand, the counter-oscillator 20, and, consequently, also the transducer housing 100, are kept small, and, in spite of this, exciter coil 41a is easily accessible, especially also during assembly. In addition to this, another advantage of this embodiment of the exciter arrangement 40 is that possibly used coil cups 41d, whose weight especially at nominal widths above 80 mm is no longer negligible, can be fixed likewise on the counter-oscillator 20 and, consequently, have practically no influence on the eigenfrequencies of the measuring tube 10. It is, however, to be noted here that, if needed, the exciter coils 41a can also be held by the counter-oscillator 20, and, then the armature 41b is held by the measuring tube 10.

In corresponding manner, the oscillation sensors 17, 18 can also be so designed and arranged in the transducer that vibrations of the measuring tube 10 and counter-oscillator 20 are differentially registered by them. In the embodiment shown in FIG. 5, the sensor arrangement 50 includes a sensor coil 51a fixed on the measuring tube 10, here located outside of all principle axes of inertia of the sensor arrangement 50. The sensor coil 51a is located as near as possible to an armature 51b fixed on the counter-oscillator 20 and so magnetically coupled with this armature 51b that a measurement voltage is induced in the sensor coil and varies as a function of rotational and/or lateral, relative movements between measuring tube 10 and counter-oscillator 20, when they change their relative position and/or relative separation. On the basis of such an arrangement of the sensor coil 51a, both the above-mentioned torsional oscillations and also the excited bending oscillations can be advantageously simultaneously registered. If required, the sensor coil 51a can, however, also be fixed for this purpose on the counter-oscillator 20, and, in corresponding manner, the armature 51b coupled therewith fixed on the measuring tube 10.

In another embodiment of the invention, measuring tube 10, counter-oscillator 20, and the sensor- and exciter-arrangements 40, 50 affixed thereto, are so matched to one another with respect to their mass distributions, that the so-formed internal part of the transducer, suspended by means of the inlet and outlet tube pieces, exhibits a center of mass MS, which lies at least inside of the measuring tube 10, preferably, however, as near as possible to the measuring tube longitudinal axis L. Furthermore, the internal part is advantageously so constructed, that it exhibits a first principle axis of inertia $T_1$ aligned with the inlet tube piece 11 and the outlet tube piece 12 and at least sectionally lying inside of the measuring tube 10. Because of the displacement of the center of mass MS of the internal part, especially, however, also because of the above-described position of the first principle axis of inertia $T_1$, the two oscillation forms assumed during operation by the measuring 10 and substantially compensated by the counter-oscillator 20, namely the torsional oscillations and the bending oscillations of the measuring tube 10, are mechanically decoupled from one another to the greatest extent possible; see, in this connection, also the WO-A 03/095950. In this way, both oscillation forms, thus lateral oscillations and/or torsional oscillations, can, without more, be advantageously excited separately from one another. Both the displacement of the center of mass MS and also the first principle axis of inertia $T_1$ towards the longitudinal axis L of the measuring tube can, for example, be considerably simplified, when the internal part, thus measuring tube 10, counter-oscillator 20, and the sensor- and exciter-arrangements 50, 40 affixed thereto, are so constructed and arranged with respect to one another that a mass distribution of the internal part along the longitudinal axis L of the measuring tube is essentially symmetrical, at least, however, invariant, with respect to an imagined rotation about the longitudinal axis L of the measuring tube by 180° (c2-symmetry). In addition, the, here, tube-shaped, especially also predominantly axial-symmetric, counter-oscillator 20 is arranged essentially coaxially with the measuring tube 10, so that the achievement of a symmetrical mass distribution of the internal part is considerably simplified and, consequently, the center of mass MS is shifted in simple manner near to the longitudinal axis of the measuring tube. Moreover, the sensor- and exciter-arrangements 50, 40 in the embodiment are so constructed and arranged with respect to one another on the measuring tube 10 and perhaps also on the counter-oscillator 20, that a mass moment of inertia is formed as concentrically as possible with the longitudinal axis L of the measuring tube, or, at least, kept as small as possible. This can e.g. be achieved such that a common center of mass of sensor- and exciter-arrangements 50, 40 lies likewise as near as possible to the longitudinal axis L of the measuring tube and/or that a total mass of sensor- and exciter arrangements 50, 40 is kept as small as possible.

In a further development of the invention, the exciter arrangement 40, for the purpose of separated excitement of torsional- and/or bending-oscillations of the measuring tube 10, is so constructed and so fixed to tube 10 and to the counter-oscillator, that a force producing the bending oscillations acts on the measuring tube along an imaginary force line extending outside of a second principle axis of inertia $T_2$ perpendicular to the first principle axis of inertia $T_1$ or cutting the former in at most one point. Preferably, the inner part is so developed, that the second principle axis of inertia $T_2$ essentially coincides with the above-mentioned central axis. In the embodiment shown in FIG. 4, the exciter arrangement 40 has for this purpose at least one exciter coil 41a, which contains in operation, at least at times, the exciter current or an exciter current component and which is fixed to a lever 41c connected to the measuring tube 10 and, by way of the lever and an armature fixed from the outside to the counter-oscillator 20, acts differentially on the measuring tube 10 and the counter-oscillator 20. The arrangement has, among other things, also the advantage that, on the one hand, the counter-oscillator 20, and, consequently, also the transducer housing 100, are kept small, and, in spite of this, exciter coil 41a is easily accessible, especially also during assembly. In addition to this, another advantage of this embodiment of the exciter arrangement 40 is that possibly used coil cups 41d, whose weight especially at nominal widths above 80 mm is no longer negligible, can be fixed likewise on the counter-oscillator 20 and, consequently, have practically no influence on the eigenfrequencies of the measuring tube 10. It is, however, to be noted here that, if needed, the exciter coils 41a can also be held by the counter-oscillator 20, and, then the armature 41b is held by the measuring tube 10.

In a further development of the invention, the exciter arrangement 40 has at least one, second exciter coil 42a arranged along a diameter of the measuring tube 10 and coupled with the measuring tub 10 and the counter-oscillator 20 in the same way as the exciter coil 41a. In another preferred development of the invention, the exciter arrangement has two further exciter coils 43a, 44a, thus at least four, arranged symmetrically with reference to the second principle axis of inertia $T_2$ and all mounted in the transducer in the previously described manner. The force acting on the measuring tube 10 outside of the second principle axis of inertia $T_2$ can be produced by means of such two- or four-coil arrangements in simple manner, e.g. by providing one of the exciter coils, e.g. the exciter coil 41a, with a different inductance as compared with, in each case, the other, or by having one of the exciter coils, e.g. the exciter coil 41a, contain in operation an exciter current component that is different from, in each case, an exciter current component of, in each case, the other exciter coils.

In another development of the invention, the sensor arrangement 50 includes, as shown schematically in FIG. 5, a sensor coil 51a fixed on the measuring tube 10 and arranged outside of the second principle axis of inertia $T_2$. The sensor coil 51a is located as near as possible to an armature 51b fixed on the counter-oscillator 20 and so magnetically coupled with this armature 51b that a measurement voltage is induced in the sensor coil and varies according to rotational and/or lateral, relative movements between measuring tube 10 and counter-oscillator 20 as they change their relative position and/or relative separation. On the basis of such an arrangement of the sensor coil 51a, both the above-mentioned torsional oscillations and also the excited bending oscillations can be advantageously simultaneously registered. If required, the sensor coil 51a can, however, also be fixed for this purpose on the counter-oscillator 20, and, in corresponding manner, the armature 51b coupled therewith fixed on the measuring tube 10.

It is noted here, further, that the exciter arrangement 40 and the sensor arrangement 50 can be constructed to have essentially equal mechanical structures in the manner known to those skilled in the art; consequently, the above-described embodiments of the mechanical structure of the exciter arrangement 40 can essentially be transferred to the mechanical structure of the sensor arrangement 50, and vice versa.

For causing the measuring tube 10 to vibrate, the exciter arrangement 40 is, as already mentioned, fed by means of a likewise oscillating exciter current $i_{exc}$, especially one oscillating at more than one frequency, of adjustable amplitude and adjustable exciter frequency $f_{exc}$, in such a manner that the exciter coils 26, 36 are traversed by such during operation and the magnetic fields required for moving the armatures 27, 37 are correspondingly produced. The exciter current $i_{exc}$ can e.g. be harmonic, multi-frequency or even rectangular. The lateral oscillation exciter frequency $f_{excL}$ of a lateral current-component $i_{excL}$ of the exciter current needed to maintain the lateral oscillations of the measuring tube 10 can be selected and adjusted in the transducer shown in the embodiment advantageously such that the laterally oscillating measuring tube 10 oscillates preferably in a bending oscillation, fundamental mode with a single oscillation antinode. Analogously thereto, also a torsional oscillation exciter frequency $f_{excT}$ of a torsional current-component $i_{excT}$ of the exciter current $i_{exc}$ needed to maintain the torsional oscillations of the measuring tube 10 can be selected and adjusted in the transducer shown in the embodiment advantageously such that the torsionally oscillating measuring tube 10 oscillates preferably in a torsional oscillation, fundamental mode with a single oscillation antinode.

For the above-described case, that the lateral oscillation frequency $f_{excL}$ and the torsional oscillation frequency $f_{excT}$, with which the measuring tube is caused to oscillate during operation, are adjusted to be different from one another, a separation of the individual oscillation modes can occur both in the exciter signals and in the sensor signals in simple and advantageous manner by means of the transducer, even in the case of simultaneously excited torsional and bending oscillations, e.g. based on a signal filtering or a frequency analysis.

For producing and adjusting the exciter current $i_{exc}$, the measuring device electronics 50 includes a suitable driver circuit 53, which is controlled by a lateral oscillation frequency setting signal $y_{FML}$ representing the lateral oscillation exciter frequency $f_{excL}$, and by a lateral oscillation amplitude setting signal $y_{AML}$ representing the lateral oscillation amplitude, which are to be set for the exciter current $i_{exc}$ and/or the lateral current-component $i_{excL}$, as well as, at least at times, by a torsional oscillation frequency setting signal $y_{FMT}$ representing the torsional oscillation exciter frequency $f_{excT}$, and by a torsional oscillation amplitude setting signal $y_{AMT}$ representing the torsional oscillation amplitude, which are to be set for the exciter current $i_{exc}$ and/or the torsional current-component $i_{excT}$. The driver circuit can be embodied e.g. by means of a voltage-controlled oscillator and a voltage-to-current converter connected downstream; instead of an analog oscillator, however, e.g. also a numerically controlled, digital oscillator can be used for adjusting the instantaneous exciter current $i_{exc}$, or the components $i_{excL}$, $i_{excT}$, of the exciter current.

For producing the lateral oscillation amplitude setting signal $y_{AML}$ and/or the torsional oscillation amplitude setting signal $y_{AMT}$, e.g. an amplitude regulation circuit 51 can be integrated into the measuring device electronics 50. Circuit 51 updates the amplitude adjusting signals $y_{AML}$, $y_{AMT}$ on the basis of instantaneous amplitudes of at least one of the two oscillation measurement signals $s_1$, $s_2$, measured at the instantaneous lateral oscillation frequency and/or the instantaneous torsional oscillation frequency, as well as on the basis of suitable, constant or variable amplitude reference values for the lateral, respectively the torsional, oscillations $W_B$, $W_T$; if necessary, also instantaneous amplitudes of the exciter current $i_{exc}$ can be introduced for generating the lateral oscillation amplitude adjustment signal $y_{AMT}$ and/or the torsional oscillation amplitude adjustment signal $y_{AMT}$; compare FIG. 7. Construction and functioning of such amplitude regulating circuits are likewise known to those skilled in the art. As an example for such an amplitude regulating circuit, reference is also made to measurement transmitters of the series "PROMASS 80", such as are offered by the assignee, for example in connection with measuring transducers of the series "PROMASS I". Its amplitude regulating circuit is preferably so designed, that the lateral oscillations of the measuring tube 10 are regulated to a constant (thus also independent of the density ρ) amplitude.

The frequency regulating circuit 52 and the driver circuit 53 can e.g. be embodied as a phase-locked loop, which is used in the manner known to those skilled in the art, for continuously adjusting the lateral oscillation frequency setting signal $y_{FML}$ and/or the torsional oscillation frequency setting signal $y_{FMT}$ to the instantaneous eigenfrequencies of the measuring tube 10 on the basis of a phase difference measured between at least one of the oscillation measurement signals $s_1$, $s_2$ and the exciter current $i_{exc}$ to be adjusted, respectively the exciter current $i_{exc}$ as instantaneously measured. The construction and use of such phase-locked loops for driving measuring tubes at their mechanical eigenfrequencies is e.g. described in detail in U.S. Pat. No. 4,801,897. Of course, also other frequency regulation circuits known to those skilled in the art can be used, such as e.g. that of U.S. Pat. No. 4,524,610 or 4,801,897. Additionally, reference is made to the already mentioned measurement transmitters of the series "PROMASS 80" regarding an application of such frequency regulating circuits for vibratory measuring transducers. Other circuits suited as driver circuits can also be taken, for example, from one of the U.S. Pat. No. 5,869,770 or 6,505,519.

In another embodiment of the invention, the amplitude regulating circuit 51 and the frequency regulating circuit 52 implemented, as schematically illustrated in FIG. 7, by means of a digital signal processor DSP provided in the measuring device electronics 50 and by means of program code correspondingly implemented, and running, in the DSP. The program code can be stored persistently or even permanently e.g. in a non-volatile memory EEPROM of a microcomputer 55 controlling and/or monitoring the signal processor and can be loaded during booting of the signal processor DSP into a volatile data-storing RAM of the measuring device electronics 50 e.g. integrated in the signal processor DSP. Signal processors for such applications are available commercially, e.g. those of type TMS320VC33 of Texas Instruments. It is, of course, practically self-evident that the oscillation measurement signals $s_1$, $s_2$ are to be converted into corresponding digital signals by means of corresponding analog-to-digital converters A/D for processing in the signal processor DSP; see EP-A 866,319 in this connection. Should it be necessary, the adjusting signals issued by the signal processor, such as e.g. the amplitude adjusting signals $y_{AML}$, $y_{AMT}$, or the frequency adjusting signals $y_{FML}$, $y_{FMT}$, can be converted in corresponding manner from digital to analog.

As illustrated in FIG. 7, the oscillation measurement signals $s_1$, $s_2$ are additionally fed to a measuring circuit 21 of the measuring device electronics. The measuring circuit 21, which is at least partially constructed to function as a flow rate computer, serves, in manner known per se to those skilled in the art, for determining, on the basis of a phase difference detected between the two, if necessary suitably pre-conditioned, oscillation measurement signals $s_1$, $s_2$, a mass flow rate measurement value $X_m$ corresponding to the mass flow rate to be measured. Suitable to serve as the measuring circuit 21 are conventional, especially digital, measuring circuits, which determine mass flow rate on the basis of oscillation measurement signals $s_1$, $s_2$; see, in this connection, the initially mentioned WO-A 02/37063, WO-A 99/39164, or the U.S. Pat. Nos. 5,648,616 and 5,069,074. Of course, also usable are other measuring circuits known to those skilled in the art to be suitable for Coriolis mass flow rate measuring devices for measuring and appropriately evaluating the phase- and/or time-differences between oscillation measurement signals of the described kind. Measurement circuit 21 also serves for producing a density measurement value $X_\rho$ representing an instantaneous density ρ of the medium or a phase of the medium.

As already mentioned at the start, inhomogeneities and/or the formation of first and second phases in the flowing medium, for example gas bubbles and/or solids particles entrained in liquids, can mean that the measurement value determined in the usual way assuming a single phase and/or homogeneous medium may not agree sufficiently accurately with the actual mass flow rate, i.e. it must be accordingly corrected. This initially determined measurement value, which provisionally represents the mass flow rate or at least corresponds therewith, and which, in the simplest case, can be a phase difference measured between the oscillation measurement signals $s_1$, $s_2$, is, therefore, referred to in the following as a first intermediate value $X'_m$. The mass flow rate measurement value $X_m$ representing the mass flow rate sufficiently accurately is finally derived by the evaluation electronics 21 from this first intermediate value $X'_m$. There is already discussion in the state of the art concerning this, that such inhomogeneities in the medium immediately affect, besides the phase difference measured between the two oscillation measurement signals $s_1$, $s_2$, also the oscillation amplitude and the oscillation frequency of each of the two oscillation measurement signals, respectively the exciter current, and, consequently, practically every operational parameter usually measured, directly or indirectly, in the use of measuring devices of the described type. This is true, in fact, especially, as also explained in WO-A 03/076880 or U.S. Pat. No. 6,505,519, for the operational parameters determined in the case of laterally oscillating measuring tubes; it can, however, also not always be excluded for those operational parameters which are measured with torsionally oscillating measuring tubes; see, in this connection, especially U.S. Pat. No. 4,524,610.

Advanced investigations on the part of the inventors have led, however, to the surprising discovery that, while the instantaneous exciter current $i_{exc}$ and, concomitantly, a damping of the oscillations of the measuring tube usually also measured during operation of the measuring device and/or a viscosity of the medium measured during operation, depend to a considerable degree on the amount of the inhomogeneity of the two- or more-phase medium and/or on a concentration of a second phase of the same, and, for example, thus from an eruption, a distribution and/or an amount of the gas bubbles and/or solids particles entrained in a liquid to be measured, nevertheless both for lateral and for torsional oscillations—at least in the above-mentioned fundamental modes—a largely reproducible and, consequently, at least experimentally determinable relationship can be postulated between the instantaneous exciter current $i_{exc}$ or an, in each case, effective component $i_{excL}$, $i_{excT}$ of the same and the degree of the inhomogeneity of the two or more-phase medium or the concentration of a second phase, especially a second phase acting as an interference. Additionally, it has been discovered, surprisingly, that a correction of the intermediate value $X'_m$ can be performed, taking into consideration the actual viscosity of the medium to be measured, respectively the phase of the medium mainly to be measured, and taking the exciter current $i_{exc}$ into consideration, which, it is recognized, can serve as a measure of an apparent viscosity or also a viscosity-density product of the medium guided in the measuring tube 11, or on the basis of at least a component $i_{excL}$, $i_{excT}$ of the exciter current required for maintaining the instantaneous oscillations of the measuring tube.

For the exact measurement of mass flow rate, even in the case of two- or more-phase medium, a second, especially digital, intermediate value $X_2$ is formed during operation by means of the measuring device electronics 2 on the basis of the exciter current $i_{exc}$, especially the regulated exciter current, and/or a component $i_{excL}$, $i_{excT}$ thereof. The second intermediate value $X_2$ corresponds to a damping of the oscillations of the measuring tube 11. This damping is a function of an apparent viscosity and/or a viscosity-density product of the medium guided in the measuring tube 11. Additionally, a correction value $X_K$, especially likewise a digital value, is determined for the intermediate value $X'_m$ by the measuring circuit 21 by using the second intermediate value $X_2$ and taking into consideration an initially suitably determined viscosity measurement value $X_\eta$, which corresponds to the actual viscosity of the medium guided in the measuring tube 11 or at least to a reference viscosity predetermined for the medium. The correction of the intermediate value $X'_m$ on the basis of the correction value $X_K$ and the generating of the mass flow rate measurement value $X_m$ can occur in the measuring device electronics for example based on the mathematical relationship $$X_m = K_m \cdot (1 + X_K) \cdot X'_m \quad (1)$$

In an embodiment of the invention, the correction value $X_K$ is determined by means of the measuring device electronics based on the mathematical relationship $$X_K = K_K \cdot (X_2 - X_\eta) \quad (2)$$

so that this is practically a measure for a deviation $\Delta\eta$ of the viscosity $\eta$ of the medium from an apparent viscosity $\eta^*$ of the medium guided in the measuring tube, as determined during operation on the basis of the exciter current $i_{exc}$ and/or a component of the exciter current $i_{exc}$, and/or from a viscosity-density product $\eta\rho$ of the medium guided in the measuring tube, as determined during operation on the basis of the exciter current $i_{exc}$. Alternatively, or as a supplement thereto, the correction value $X_K$ can be determined, furthermore, on the basis of the mathematical relationship $$X_K = K'_K \cdot \left(1 - \frac{X_\eta}{X_2}\right) \quad (3)$$

Thus, while, in Equation (2), the correction value $X_K$ Is determined on the basis of a difference $\Delta\eta$ existing between the intermediate value $X_2$ and the viscosity measurement value $X_\eta$, which corresponds, in turn, practically to an absolute error between the two measured values, Equation (3) determines the correction value $X_K$ on the basis of a comparison of the second intermediate value $X_2$ with the viscosity measurement value $X_\eta$ or also on the basis of a relative error $\Delta\eta/\eta^*$ between the two measured values $X_2$, $X_\eta$. In this respect, the correction value $X_K$ represents, at least for a two-phase medium, also a measure for an instantaneous, relative or absolute concentration of a first or a second phase of the medium, especially for gas bubbles in a liquid. Besides the generating of the mass flow rate measurement value $X_m$, the intermediate value $X_2$ can, consequently, also be used advantageously, additionally, e.g. for signaling, e.g. on site or in a remote control room, in visually observable manner, the degree of inhomogeneity of the medium or measurements derived therefrom, such as e.g. a percent air content in the medium or a volume-, quantity-, or mass-fraction of solids particles entrained in the medium.

Figure 9:
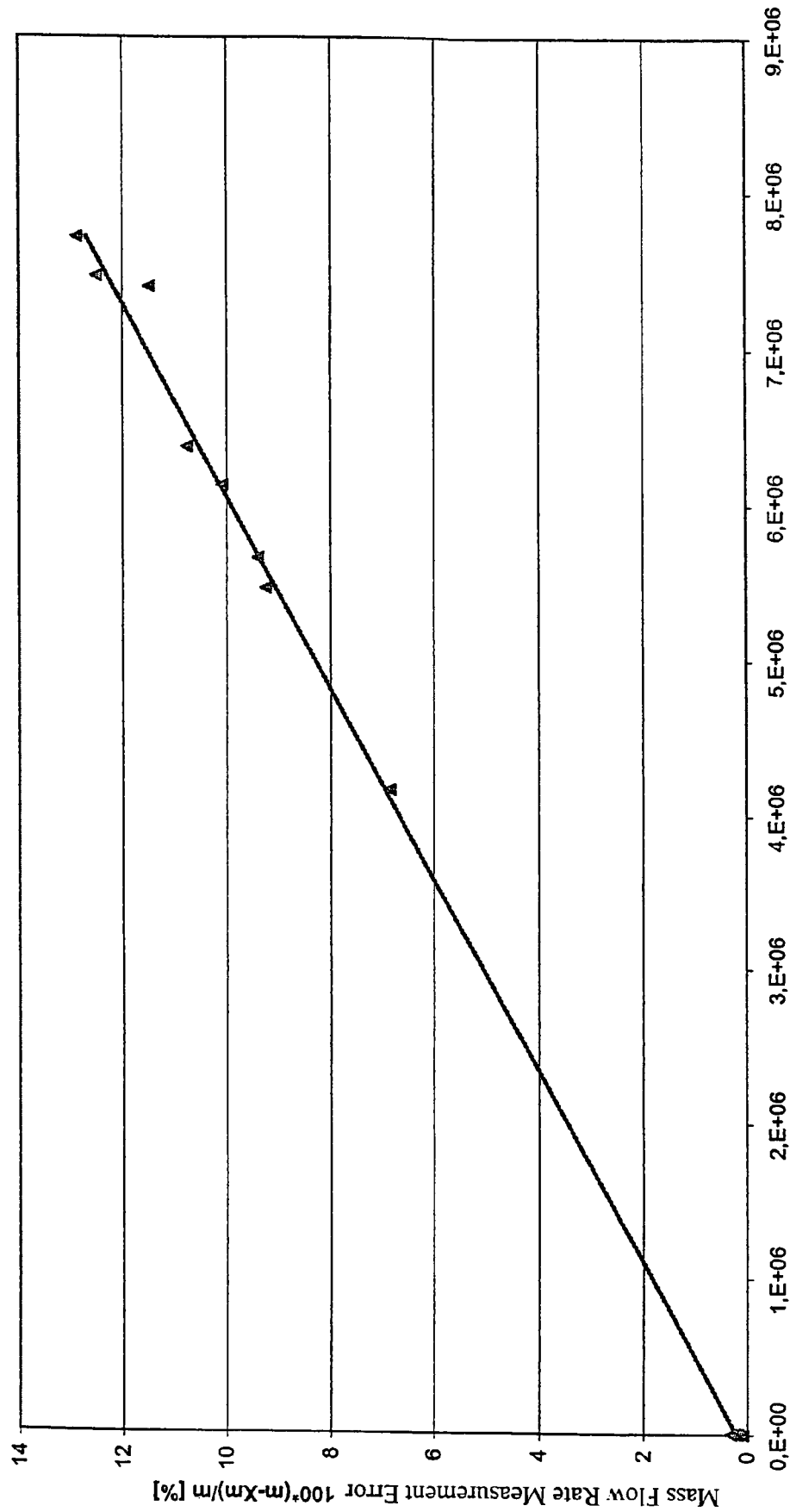

Additional experimental investigations have shown that, for a transducer according to the illustrated example of an embodiment, consideration of the instantaneous lateral oscillation frequency of the vibrating measuring tube can lead to a further improvement of the accuracy of the mass flow rate measurement value $X_m$. Moreover, a normalizing of the correction value $X_K$ determined from Equation (2) or (3) with the square root of the instantaneous lateral oscillation frequency can achieve that the correction value $X_K$ is essentially proportional to the gas fraction, at least for the case that a liquid, for example glycerin, is to be measured having entrained gas bubbles, for example air; reference, in this connection, also FIG. 9. Thus, according to a further development of the invention, Equation (2) is modified using a lateral oscillation frequency measurement value $X_{fexcL}$ representing the instantaneous lateral oscillation frequency, as follows:

$$X_K = K_K \cdot \frac{(X_2 - X_\eta)}{\sqrt{X_{fexcL}}} \quad (4)$$

The determining of the lateral oscillation frequency measurement value can occur in simple manner, e.g. on the basis of the above-mentioned lateral oscillation frequency regulating signal $y_{FML}$.

It is known that the damping of the oscillations of the measuring tube 10 is determined not only by a damping component attributable to viscous friction within the medium, but also by a damping component practically independent of the medium. This latter component is caused by mechanical friction forces, which e.g. act in the exciter arrangement 40 and in the material of the measuring tube 10. Stated differently, the instantaneously measured exciter current $i_{exc}$ represents the totality of the frictional forces and/or frictional torques in the transducer 10, including both the mechanical frictions in the transducer and the viscous friction in the medium. In the determining of the intermediate value $X_2$, which, as already mentioned, should correspond mainly with the damping attributable to viscous frictions in the medium, the medium-independent, mechanical damping component is to be appropriately considered, especially appropriately separated out, or eliminated.

For determining the intermediate value $X_2$, one embodiment of the invention thus provides that there is subtracted from a total exciter current measurement value $X_{iexc}$, especially a digital such value, instantaneously representing the exciter current $i_{exc}$, and/or from a lateral current measurement value $X_{iexcL}$, especially a digital such value, instantaneously representing the lateral current component $i_{excL}$, and/or from a torsional current measurement value $X_{iexcT}$, especially a digital such value, instantaneously representing the torsional current component $i_{excT}$, in each case a correspondingly associated total empty current measurement value $K_{iexc}$, lateral empty current measurement value $K_{iexcL}$, respectively a torsional empty current measurement value $K_{iexcT}$, of which each represents the mechanical friction forces arising in the transducer in the case of empty measuring tube 10. Each of the empty current measurement values $K_{iexc}$, $K_{iexcL}$, $K_{iexcT}$ is likewise to be determined during a calibration of the Coriolis mass flow rate measuring device, e.g. for an evacuated measuring tube 10, or one carrying only air, and appropriately stored or installed in the measurement device electronics 50, especially as normalized to the oscillation amplitude associated therewith. It is clear, without further explanation, for one skilled in the art that, if required, other physical parameters influencing the empty current measurement values $K_{iexc}$, $K_{iexcL}$, $K_{iexcT}$, parameters such as e.g. an instantaneous temperature of the measuring tube and/or medium, can be considered in their calibration. For calibrating the measuring transducer 10, usually two or more, different, two- or more-phase media having varying, but known, flow parameters, such as e.g. known concentrations of the individual medium phases of the calibrating medium, its density $\rho$, mass flow rate m, viscosity $\eta$ and/or temperature, are caused to flow serially through the measuring transducer 10 and the corresponding reactions of the measured value transducer 10, reactions such as the instantaneous exciter current $i_{exc}$, the instantaneous lateral oscillation exciter frequency $f_{excL}$ and/or the instantaneous torsional oscillation exciter frequency $f_{excT}$, are measured. The set flow parameters and each measured reaction of the measured operational parameters of the measuring transducer 10 are matched appropriately to one another and, consequently, mapped for the corresponding calibration constants. For example, for determining the constants in the case of the calibration measurement for two calibration media of known viscosity held as constant as possible and of inhomogeneity developed in different, but in each case unchanging, manner, a ratio $X_m'/m$ and/or $X_m/m$ is formed, of the, in each case, determined intermediate value $X_m'$, respectively of the, in each case, determined mass flow rate measurement value $X_m$, to the, in each case, current mass flow rate at known air fraction. For example, the first calibrating medium can be flowing water, or even oil, with entrained air bubbles, and the second calibration medium can be water, or even oil, which is as homogeneous as possible. The determined calibration constants can then be e.g. stored in the form of digital data in a table memory of the measuring device electronics; they can, however, also serve as analog setting values for corresponding computational circuits. It is to be noted here that the calibration of measuring transducers of the described type is known, per se, to those skilled in the art, or at least to be comprehended on the basis of the above explanations and, consequently, no further explanation is required. Advantageously, for determining the total exciter current measurement $X_{iexc}$, the lateral current measurement $X_{iexcL}$ and/or the torsional current measurement $X_{iexcT}$, the already mentioned lateral oscillation amplitude setting signal $y_{AML}$ and/or the torsional oscillation amplitude setting signal $y_{AMT}$ can be used, since these represent the exciter current $i_{exc}$ or its components $i_{excL}$, $i_{excT}$ sufficiently accurately for the correction.

Figure 8:
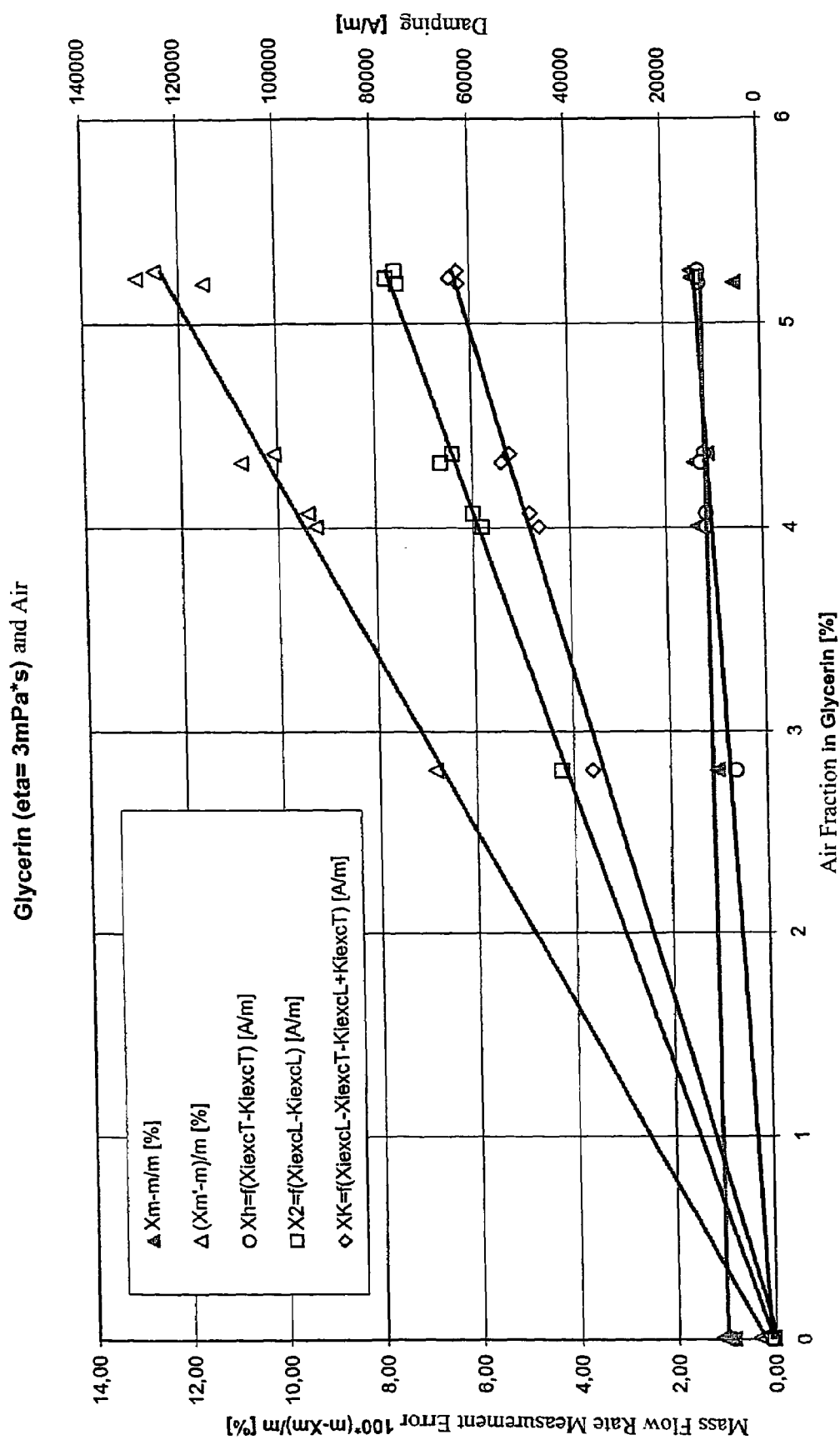

In a further embodiment of the invention, the determining of the correction value therein occurs, as also shown in FIG. 8, by way of example, using experimentally determined current measurement values $X_{iexcL}$, $X_{iexcT}$ and empty current measurement values $K_{iexcL}$, $K_{iexcT}$, on the basis of the lateral current component $i_{excL}$ driving the lateral oscillations and on the basis of the associated lateral empty current measurement value $K_{iexcL}$, especially based on the mathematical relationship $$X_2 = K_2 \cdot (X_{iexcL} - K_{iexcL}) \tag{5}$$

and/or based on the mathematical relationship $$X_2 = K_2' \cdot \left(1 - \frac{K_{iexcL}}{X_{iexcL}}\right) \tag{6}$$

In case necessary, especially in the case of oscillation amplitudes of the vibrating measuring tube significantly varying during operation and/or deviating from the calibrated reference values, the lateral current component $i_{excL}$ can initially likewise be normalized on the instantaneous oscillation amplitude of the lateral oscillations of the measuring tube, for example using the oscillation measurement signals $s_1$, $s_2$.

In a further embodiment of the invention, the viscosity measurement value $X_\eta$ represents a predetermined reference viscosity, which is determined in advance. For example, used for this can be the viscosity measurement value based on knowledge of the medium to be measured, fed in from a remote control location or manually on site, or transmitted from an external viscosity meter to the measuring device electronics via a field bus.

In a further development of the invention, the viscosity measurement value $X_\eta$ is produced by means of the measurement electronics 2 itself.

For the above-described case, namely, that the straight measuring tube is caused to oscillate in operation simultaneously or alternatingly, laterally and torsionally, the viscosity measurement value can, however, also be determined in operation directly by Coriolis mass flow measuring device 1 using measuring transducer 1 and measuring device electronics 2. Straight measuring tubes can, as is known, when excited to torsional oscillations about a torsional oscillation axis extending parallel to, or coinciding essentially with, the measuring tube longitudinal axis, effect that shear forces are produced in the medium guided therethrough, whereby, in turn, significant oscillation energy is sapped from the torsional oscillations. As a result, a significant damping of the torsional oscillations of the oscillating measuring tube, for the maintenance of which extra electrical exciting power $P_{exc}$ must be fed to the measuring tube. Using the electrical exciting power $P_{excT}$ needed for maintaining the torsional oscillations of the measuring tube 10, those skilled in the art can, in known manner, make use of the measuring transducer to determine, at least approximately, also the viscosity η of the medium; see, in this connection, especially also any one of the U.S. Pat. Nos. 4,524,610, 5,253,533, 6,006,609 and 6,651,513.

It has been found, surprisingly, that, in spite of that fact that both the exciter current $i_{exc}$, or lateral current component $i_{excL}$ needed for maintaining the lateral oscillations of the measuring tube 10 and, as discussed especially in U.S. Pat. No. 4,524,610 or EP-A 1 291 639, the exciter current $i_{exc}$ or torsional current component $i_{excT}$ needed for maintaining the torsional oscillations of the measuring tube 10 are dependent to a significant degree on the degree of the inhomogeneity or on the concentrations of the individual medium phases, the inclusion of the viscosity measurement value $X_η$ produced in the above-described manner by means of the Coriolis mass flow measuring device 1 itself enables an amazingly robust and very well reproducible correction of the intermediate value $X'_m$ and, consequently, also the generating of a very accurate mass flow rate measurement value $X_m$.

Thus, in a first variant of this further development of the invention, wherein also the viscosity measurement value $X_η$ is produced by means of the measuring device electronics 2, this is determined on the basis of the exciter current $i_{exc}$ driving the exciter arrangement 40 in the case of the measuring tube oscillating at least partially torsionally, especially on the basis of the torsional current component $i_{excT}$ serving for maintaining the torsional oscillations of the measuring tube 10. Moreover, also the intermediate value $X_2$ and/or the correction value $X_K$ are/is calculated based on this internally determined viscosity measurement value $X_η$. Taking into consideration the relationship already described in U.S. Pat. No. 4,524,610:

$$\sqrt{η} \sim i_{excT}, \quad (7)$$

according to which the torsional current component $i_{excT}$ reduced by the above-mentioned torsional empty current measurement value $K_{iexcT}$ correlates very well with the square root of the actual viscosity η, at least in the case of constant density ρ, correspondingly for determining the viscosity measurement value $X_η$, first, internally in the measuring device electronics, a squared value $X^2_{\Delta iexcT}$ is formed from the torsional current measurement value $X_{iexcT}$ derived from the exciter current $i_{exc}$, reduced by the torsional empty current measurement value $K_{iexcT}$. Starting there, the viscosity measurement value $X_η$ is numerically determined, according to a further embodiment of the invention, based on the mathematical relationship:

$$X_η = K_η \cdot \frac{X^2_{\Delta iexcT}}{X_ρ}. \quad (8)$$

where $K_η$ is a device constant, especially one also dependent on the geometry of the measuring tube 10. The density measurement value $X_ρ$ appearing in the denominator of the formula merely cares for the fact that the square of the current actually provides information on the product of density and viscosity; see also, in this connection, U.S. Pat. No. 4,524,610.

The viscosity measurement value $X_η$ determined according to this mathematical relationship provides a good approximation for a dynamic viscosity of the fluid, which, as is known, can be formed also as the product of kinematic viscosity and density, ρ, of the fluid. If the viscosity measurement value $X_η$ is to serve as an approximation of the kinematic viscosity, then, before its output, a corresponding normalizing must be done on the density measurement value $X_ρ$, e.g. by means of a simple numerical division. For this purpose, Equation (8) can be modified as follows:

$$X_η = K_η \cdot \left(\frac{X_{\Delta iexcT}}{X_ρ}\right)^2 \quad (9)$$

In a further embodiment of the invention, the square $X^2_{iexcT}$ of the torsional current measurement value $X_{iexcT}$ is normalized for forming the viscosity measurement value $X_η$ by means of a simple numerical division on an amplitude measurement value $X_{sT}$, which represents an instantaneous, operationally possibly varying signal amplitude of at least one of the oscillation measurement signals $s_1$, $s_2$, in the case of a torsionally oscillating measuring tube. Thus, it has been found, additionally, that, for such viscosity measuring devices using such a vibratory transducer, and especially also at constantly regulated oscillation amplitude and/or at simultaneous excitation of lateral and torsional oscillations, a ratio $i_{exc}/θ$ of the exciter current $i_{exc}$ to a practically not-directly measurable velocity of a movement causing the internal frictions and thus also the frictional forces in the medium is a more accurate approximation for the already mentioned damping opposing the deflections of the measuring tube 10. Therefore, for further increasing the accuracy of the viscosity measurement value $X_η$, especially however also for decreasing its sensitivity to fluctuating oscillation amplitudes of the vibrating measuring tube 10 possibly occurring during operation, it is further provided that, for determining the viscosity measurement value $X_η$, the torsional current measurement value $X_{iexcT}$ is first normalized on the amplitude measurement value $X_{sT}$, which represents, with sufficient accuracy, the above-mentioned velocity θ. Stated differently, a normalized torsional current measurement value $X'_{iexcT}$ is formed using the following formula:

$$X'_{iexcT} = \frac{X_{iexcT}}{X_{sT}} \quad (10)$$

The amplitude measurement value $X_{s1}$ is preferably derived from the at least one, possibly already digitized, sensor signal $s_1$ by means of the measuring device electronics 50, e.g. by means of an internal amplitude measurement circuit, based on the recognition that the motion causing the viscous friction in the medium corresponds very strongly with the movement of the vibrating measuring tube 10 registered by means of the sensor 51 or also locally registered by means of the sensor 51. Using the normalized torsional current measurement value $X'_{iexcT}$, the viscosity measurement value can then be determined e.g. according to the following formula:

$$X_\eta = K_\eta \cdot \frac{X_{iexcT}^{\prime 2}}{K_f \cdot X_p} \quad (11)$$

The correction factor $K_f$ introduced in this equation serves solely to weight the density measurement value $X_\rho$ with the current oscillation frequency of the vibrating measuring tube 10. It is noted here by way of repetition that the sensor signal $s_1$ is preferably proportional to a velocity of an especially lateral deflection movement of the vibrating measuring tube 10; the sensor signal $s_2$ can, however also be e.g. proportional to an acceleration acting on the vibrating measuring tube and to a distance traveled by the vibrating measuring tube 10. For the case where the sensor signal $s_1$ is designed in the above sense to be velocity proportional, the correction factor Kf corresponds to the oscillation frequency of the vibrating measuring tube 10, while it is e.g. equal to the third power of the oscillation frequency in the case of a distance-proportional sensor signal $s_1$.

Instead of measuring the excitation energy $E_{exc}$, or even in supplementation thereof, a further possibility for determining the viscosity of the medium is to measure and appropriately evaluate a pressure difference over a suitable measurement distance along the pipeline or along the measuring tube 10; see, in this connection, especially one of the U.S. Pat. Nos. 5,359,881 or 6,513,393. At least in the case of essentially laminar flow in the measurement section, the viscosity measurement value for the correction of the intermediate value $X'_m$ can be determined with sufficient accuracy using the following mathematical relationship:

$$X_\eta = K_p \cdot \frac{X_{\Delta p}}{X'_m} \cdot X_p \quad (12)$$

Equation (12) is based fundamentally on the known Hagen-Poiseuille law, with the calibration factor $K_p$ being an initially determinable parameter depending especially on a diameter and a length of the measurement section. For implementing this mathematical relationship, the measuring device electronics 2 is, in a second variant of this further development of the invention, in which also the viscosity measurement value $X_\eta$ is produced by means of the measuring device electronics 2, at least at times coupled with a differential pressure sensor, which at least at times delivers a pressure difference measurement value $X_{\Delta p}$ representing a pressure difference measured along the pipeline and/or along the measuring tube.

The above-presented functions serving for producing the mass flow rate measurement value $X_m$, symbolized by the Equations (1) to (12), can be implemented at least in part by means of the signal processor DSP or e.g. also by means of the above-mentioned microcomputer 55. The creation and implementation of corresponding algorithms, which correspond with the aforesaid equations or which emulate the functioning of the amplitude regulating circuit 51, respectively the frequency regulating circuit 52, as well as their translation into program code executable in such signal processors, is familiar per se to those of ordinary skill in the art and, thus, does not, at least when knowing the present invention, require any detailed explanation. Of course, the aforementioned equations can also be easily represented totally or partially in the measuring device electronics 50 by means of corresponding, discretely constructed, analog and/or digital calculating circuits.

In a further development of the invention, the instantaneously suitable correction value $X_K$ is determined practically directly during operation, starting from the intermediate value $X_2$, by mapping, especially programming, in the measurement device electronics a unique relationship between the current intermediate value $X_2$ and the correction value $X_K$ matched thereto. To this end, the measuring device electronics 2 has a table memory, in which a data set is initially stored, for example in the form of digital correction values $X_{K,i}$ determined during the calibration of the Coriolis mass flow rate measuring device. These correction values $X_{K,i}$ are directly accessed by the measuring circuit via a memory address derived by means of the instantaneously valid, second intermediate value $X_2$. The correction value $X_K$ can e.g. be determined in simple manner by comparing the instantaneously determined intermediate value $X_2$ with corresponding default values for the intermediate value $X_2$ entered in the table memory and reading out, and thus using from the evaluation electronics 2 for the further calculation, that correction value $X_{K,i}$ that corresponds to the default value coming closest to the intermediate value $X_2$. Serving as table memory can be a programmable, read only memory, thus a FPGA (field programmable gate array), an EPROM or an EEPROM. The use of such a table memory has, among others, the advantage that the correction value $X_K$ is very rapidly available during run time following calculation of the intermediate value $X_2$. Furthermore, the correction values $X_{K,i}$ entered in the table memory can be initially determined very accurately, e.g. based on the Equations (2), (3) and/or (4), and by application of the method of least squares.

As is evident on the basis of the above explanations, a correction of the intermediate value $X'_m$ can be carried out using fewer, very simply determinable, correction factors. On the other hand, the correction can be performed using the initially determined viscosity measurement value $X_\eta$, and the initially determined intermediate value $X'_m$, with a calculation burden small in comparison to the initially mentioned, more complex calculational method. An additional advantage of the invention is that at least some of the aforementioned correction factors can be derived without difficulty from the flow parameters determined by means of Coriolis mass flow rate measuring devices, especially from the measured density and/or the—here provisionally—measured mass flow rate, and/or from the operational parameters usually directly measured in the operation of Coriolis mass flow rate measuring devices, especially the measured oscillation amplitudes, oscillation frequencies and/or the exciter current itself.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A coriolis mass flow measuring device, especially a Coriolis mass flow rate/density measuring device, or a Coriolis mass flow rate/viscosity measuring device, for measuring the mass flow rate of a medium flowing in a pipeline, especially a medium of two or more phases, which Coriolis mass flow measuring device comprises:

a vibratory transducer and measuring device electronics electrically coupled to said vibratory transducer, wherein said vibratory transducer has:

at least one measuring tube to be interposed in the pipeline, especially an essentially straight measuring tube, for guiding the medium to be measured, in communication with the connected pipeline, an exciter arrangement acting on said at least one measuring tube for causing said at least one measuring tube to vibrate with lateral oscillations, especially bending oscillations, at least at times, and/or at least in part, during operation, and a sensor arrangement for registering vibrations of said at least one measuring tube, which delivers at least one, first oscillation measurement signal ($s_1$) representing oscillations of said at least one measuring tube at the inlet end and at least one, second oscillation measurement signal ($s_2$) representing oscillations of said at least one measuring tube at the outlet end, and said measuring device electronics delivers, at least at times, an exciter current ($i_{exc}$) driving the exciter arrangement and, at least at times, a mass flow rate measurement value ($X_m$) representing a mass flow rate to be measured, produces a first intermediate value ($X'_m$) derived from the oscillation measurement signals ($s_1$, $s_2$) and corresponding to the mass flow rate to be measured and/or to a phase difference between the two oscillation measurement signals ($s_1$, $s_2$), as well as a second intermediate value ($X_2$) derived from the exciter current ($i_{exc}$), and/or from a component of the exciter current ($i_{exc}$), and corresponding to a damping of the oscillations of said measuring tube, especially a damping dependent on an apparent viscosity, and/or a viscosity-density product, of the medium guided in said at least one measuring tube, and uses the second intermediate value ($X_2$) and a viscosity measurement value ($X_\eta$) predetermined, or determined during operation, especially by use of the transducer and/or the measuring device electronics, and corresponding to a viscosity of the medium guided in said at least one measuring tube and/or to a previously supplied, reference viscosity, to produce a correction value ($X_K$) for the first intermediate value ($X'_m$), and, on the basis of the first intermediate value ($X'_m$) and the correction value ($X_K$), to produce the mass flow rate measurement value ($X_m$).

2. The coriolis mass flow measuring device as claimed in claim 1, wherein:

the correction value ($X_K$) represents a deviation of the viscosity of the medium from an apparent viscosity of the medium guided in said at least one measuring tube, determined in operation on the basis of the exciter current ($i_{exc}$) and/or on the basis of a component of the exciter current ($i_{exc}$) and/or from a viscosity-density product of the medium guided in said at least one measuring tube, determined in operation on the basis of the exciter current ($i_{exc}$).

3. A coriolis mass flow measuring device as claimed in claim 1, wherein:

said measuring device electronics determines the correction value ($X_K$) on the basis of a comparison of the second intermediate value ($X_2$) with the viscosity measurement value ($X_\eta$) and/or on the basis of a difference existing between the second intermediate value ($X_2$) and the viscosity measurement value ($X_\eta$).

4. The coriolis mass flow measuring device as claimed in claim 1, wherein:

said measuring device electronics produces the second intermediate value ($X_2$) also using at least one of the oscillation measurement signals ($s_1$, $s_2$).

5. The coriolis mass flow measuring device as claimed in claim 1, wherein:

said exciter arrangement causes said at least one measuring tube at least at times and/or at least in part, during operation, to execute torsional oscillations about an imaginary measuring tube longitudinal axis essentially aligned with said at least one measuring tube, especially a principal axis of inertia of said at least one measuring tube, especially torsional oscillations alternating with the lateral oscillations or at times superimposed therewith; and said measuring device electronics also determines the viscosity measurement value ($X_\eta$) on the basis of the exciter current ($i_{exc}$), or a component of the exciter current ($i_{exc}$), driving said exciter arrangement.

6. The coriolis mass flow measuring device as claimed in claim 1, wherein:

said at least one measuring tube, derived by said exciter arrangement, executes torsional oscillations with a measuring tube torsional oscillation frequency, which is tuned to be different from a measuring tube bending oscillation frequency with which said at least one measuring tube, driven by said exciter arrangement, executes bending oscillations.

7. The coriolis mass flow measuring device as claimed in claim 1, wherein:

said measuring device electronics also produces the viscosity measurement value ($X_\eta$).

8. The coriolis mass flow measuring device as claimed in claim 1, wherein:

said measuring device electronics delivers a density measurement value ($X_\rho$) representing a density of the medium and derived from the first and/or from the second oscillation measurement signal ($s_1$, $s_2$) and;

said measuring device electronics determines the correction value ($X_K$), especially the viscosity measurement value ($X_\eta$), also on the basis of the density measurement value ($X_\rho$).

9. The coriolis mass flow measurement device as claimed in claim 1, wherein:

said measuring device electronics is coupled with an external viscosity measuring device, especially such a device arranged remotely from the Coriolis mass flow measuring device, and said external viscosity measuring device delivers, at least at times, the viscosity measurement value ($X_\eta$).

10. The coriolis mass flow measuring device as claimed in claim 1, wherein:

said measuring device electronics, at least at times, is coupled with a pressure sensor, which at least at times delivers a pressure difference measurement value ($X_{\Delta p}$) representing a pressure difference measured along the pipeline.

11. The coriolis mass flow measuring device as claimed in claim 1, wherein:

said measuring device electronics determines, at least at times, a concentration measurement value ($X_C$), which represents, in the case of a two- or more-phase medium in the measuring tube, a volume- and/or mass-fraction of a medium phase, especially a relative fraction, on the basis of the exciter current ($i_{exc}$) and/or on the basis of a component of the exciter current ($i_{exc}$), as well as with use of the viscosity measurement value ($X_\eta$).

12. The coriolis mass flow measuring device as claimed in claim 1, wherein:
said at least one measuring tube communicates with the connected pipeline via an inlet tube piece opening into an inlet end and via an outlet tube piece opening into an outlet end; and
the transducer includes, fixed at the inlet end and at the outlet end of said at least one measuring tube, especially also mechanically coupled with said exciter arrangement, a counter-oscillator, which vibrates during operation at least at times, especially with phase opposite to that of said at least one measuring tube.

13. The use of a Coriolis mass flow measuring device as claimed in claim 1 for measuring a mass flow rate of a two- or more-phase medium, especially a liquid-gas mixture, flowing in a pipeline.

14. A method for measuring a mass flow rate of a medium, especially a medium of two or more phases, flowing in a pipeline, using a Coriolis mass flow measuring device having a vibratory transducer and a measuring device electronics electrically coupled with the transducer, which method comprises the following steps:
flowing the medium to be measured through at least one measuring tube of the transducer communicating with the pipeline and feeding an exciter current ($i_{exc}$) into an exciter arrangement mechanically coupled to the measuring tube guiding the medium for causing mechanical oscillations, especially bending oscillations, of the measuring tube;
letting the measuring tube vibrate in an oscillation mode suited for producing Coriolis forces in the medium flowing therethrough;
registering vibrations of the measuring tube and producing a first oscillation measurement signal ($s_1$) representing inlet-end oscillations and a second oscillation measurement signal ($s_2$) representing outlet-end oscillations;
developing, using the two oscillation measurement signals ($s_1$, $s_2$), a first intermediate value ($X'_m$) corresponding to the mass flow rate to be measured and/or to a phase difference between the two oscillation measurement signals ($s_1$, $s_2$);
determining a second intermediate value ($X_2$) derived from the exciter current ($i_{exc}$) and corresponding to a damping of the oscillations of the measuring tube, especially a damping dependent on an apparent viscosity and/or a viscosity-density product of the medium guided in the measuring tube, producing a correction value ($X_K$) for the first intermediate value ($X'_m$) by means of the second intermediate value ($X_2$) and by means of an initially determined viscosity measurement value ($X_\eta$), especially by use of the transducer and/or the measuring device electronics, corresponding to a viscosity of the medium guided in the measuring tube;
correcting the first intermediate value ($X'_m$) by means of the correction value ($X_K$) and producing a mass flow rate measurement value ($X_m$) representing the mass flow rate to be measured.

15. The method as claimed in claim 14, comprising the following additional step of:
causing bending oscillations in the measuring tube for producing Coriolis forces in the medium flowing therethrough.

16. The method as claimed in claim 14, comprising the following additional steps of:
causing torsional oscillations in the measuring tube, especially torsional oscillations superimposed on the bending oscillations; and
determining a second intermediate value ($X_2$) taking into consideration the exciter current ($i_{exc}$ and/or at least a component of the exciter current ($i_{exc}$) causing the torsional oscillations of the measuring tube.

17. The method as claimed in claim 14, wherein the step of producing the correction value ($X_K$) for the intermediate value ($X'_m$) comprises the following further step of:
comparing the second intermediate value ($X_2$) with the viscosity measurement value ($X_\eta$) and/or determining a difference existing between the second intermediate value ($X_2$) and the viscosity measurement value ($X_\eta$); and
determining a deviation of the viscosity of the medium from an apparent viscosity of the medium guided in the measuring tube, determined during operation on the basis of the exciter current ($i_{exc}$), and/or from a viscosity-density product of the medium guided in the measuring tube, determined during operation on the basis of the exciter current ($i_{exc}$).

18. The method as claimed in claim 14, comprising the following additional steps of:
developing on the basis of the oscillation measurement signals ($s_1$, $s_2$) a second measurement value ($X_\rho$) representing a density of the medium; and
developing a correction value ($X_K$) using the second measurement value ($X_\rho$).

19. The use of the method as claimed in claim 14 for calibrating a Coriolis mass flow measuring device and/or a vibratory transducer having at least one measuring tube.

* * * * *